(12) United States Patent
Cioanta et al.

(10) Patent No.: US 8,961,441 B2
(45) Date of Patent: Feb. 24, 2015

(54) MEDICAL TREATMENT SYSTEM INCLUDING AN ANCILLARY MEDICAL TREATMENT APPARATUS WITH AN ASSOCIATED DATA STORAGE MEDIUM

(75) Inventors: Iulian Cioanta, Weston, FL (US); Rene Brauchli, Alterswilen (CH); Manfred Menzi, Buchs (CH); Christopher M. Cashman, Duluth, GA (US)

(73) Assignee: Sanuwave, Inc., Alpharetta, GA (US)

( * ) Notice: Subject to any disclaimer, the term of this patent is extended or adjusted under 35 U.S.C. 154(b) by 1072 days.

(21) Appl. No.: 12/437,411

(22) Filed: May 7, 2009

(65) Prior Publication Data

US 2010/0331741 A9     Dec. 30, 2010

Related U.S. Application Data

(60) Provisional application No. 61/051,289, filed on May 7, 2008.

(51) Int. Cl.
| | | |
|---|---|---|
| *A61H 1/00* | (2006.01) |
| *A61N 7/00* | (2006.01) |
| *A61M 37/00* | (2006.01) |
| *G06F 19/00* | (2011.01) |
| *A61B 8/00* | (2006.01) |
| *A61B 19/00* | (2006.01) |
| *A61B 18/00* | (2006.01) |

(52) U.S. Cl.
CPC ............. *A61N 7/00* (2013.01); *A61M 37/0092* (2013.01); *G06F 19/3406* (2013.01); *G06F 19/3481* (2013.01); *A61B 8/00* (2013.01); *A61B 19/44* (2013.01); *A61B 2018/00988* (2013.01); *A61B 2019/442* (2013.01); *A61B 2019/448* (2013.01); *A61N 2007/0013* (2013.01); *A61N 2007/0017* (2013.01)
USPC ............................................................ 601/2

(58) Field of Classification Search
CPC ................................... A61N 7/00; A61N 7/02
USPC ............................................................ 601/2
See application file for complete search history.

(56) References Cited

U.S. PATENT DOCUMENTS

| | | | |
|---|---|---|---|
| 4,991,604 | A | 2/1991 | Wurster et al. |
| 5,085,206 | A | 2/1992 | Mestas et al. |
| 5,156,144 | A | 10/1992 | Iwasaki et al. |
| 5,419,335 | A | 5/1995 | Hartmann et al. |
| 7,299,981 | B2 | 11/2007 | Hickle et al. |
| 2002/0193709 | A1 | 12/2002 | Bolze et al. |
| 2003/0065294 | A1* | 4/2003 | Pickup et al. ................. 604/304 |
| 2004/0254816 | A1 | 12/2004 | Myers |
| 2005/0075599 | A1* | 4/2005 | Redding, Jr. .................... 604/22 |
| 2006/0036195 | A1 | 2/2006 | Schultheiss et al. |
| 2006/0100549 | A1 | 5/2006 | Schultheiss et al. |
| 2006/0100550 | A1 | 5/2006 | Schultheiss et al. |
| 2006/0184071 | A1 | 8/2006 | Klopotek |
| 2007/0163583 | A1 | 7/2007 | Brand et al. |

(Continued)

*Primary Examiner* — Tse Chen
*Assistant Examiner* — Hien Nguyen
(74) *Attorney, Agent, or Firm* — Hunton & Williams LLP

(57) ABSTRACT

A medical treatment system includes an electronic controller with a medical treatment apparatus, a data reader, an ancillary treatment apparatus used with the electronic medical treatment apparatus and a data storage medium associated with the ancillary treatment apparatus. The controller is configured to receive information from the data storage medium, and to control the medical treatment apparatus with medical treatment parameters compatible with the desired medical treatment and the ancillary treatment apparatus.

22 Claims, 14 Drawing Sheets

(56) References Cited

U.S. PATENT DOCUMENTS

| | | |
|---|---|---|
| 2007/0213684 A1 | 9/2007 | Hickle et al. |
| 2007/0244825 A1 | 10/2007 | Semmer et al. |
| 2007/0249969 A1* | 10/2007 | Shields, Jr. .................. 601/2 |
| 2008/0004904 A1 | 1/2008 | Tran |
| 2008/0061153 A1 | 3/2008 | Hickle et al. |
| 2008/0081963 A1* | 4/2008 | Naghavi et al. ............. 600/301 |
| 2008/0097205 A1* | 4/2008 | Takimoto et al. ............ 600/437 |
| 2008/0221930 A1* | 9/2008 | Wekell et al. ................ 705/3 |
| 2009/0239710 A1* | 9/2009 | Shemesh et al. ............. 482/8 |

* cited by examiner

| | | |
|---|---|---|
| 710 | Number of Treatments | 4 |
| 712 | Length of time Each Treatment | 10 minutes |
| 714 | Total Length of Time | 2 weeks |
| 716 | Number of Shocks Each Treatment | 3000 |
| 718 | Total Number of Shocks | 6000 |
| 720 | Frequency | 0.5-4 Hz |
| 722 | Energy Setting | E1-E6 |
| 724 | Treatment Area | Wound ($cm^2$) |
| 726 | Treatment Penetration Depth | 2 cm |
| 728 | Ancillary Treatment Apparatus | Device YYY |
| 730 | Medical Treatment Apparatus | Device XXX |
| 732 | Controller | Device ZZZ |
| 734 | Region | U.S.A. |

Fig. 15

MEDICAL TREATMENT SYSTEM INCLUDING AN ANCILLARY MEDICAL TREATMENT APPARATUS WITH AN ASSOCIATED DATA STORAGE MEDIUM

CROSS-REFERENCE TO RELATED APPLICATIONS

The present application claims the benefit of priority of U.S. Provisional Application No. 61/051,289 filed May 7, 2008, which is incorporated herein by reference.

FIELD OF THE INVENTION

Embodiments of the invention relate to medical treatment, and to systems, kits, methods and computer program products for medical treatment and fee provisioning for the same.

BACKGROUND INFORMATION

Medical systems using medical treatment kits, ancillary apparatuses and treatment articles with medical treatment devices are subject to operation and billing errors of the medical personnel administering the treatment with such components. As a result, medical procedure charges may be incorrect, cross-contamination between patients using the same apparatus may occur, the wrong components may be used together or the wrong medical treatment parameters may be applied.

Accordingly, it is desirable to have a medical system and treatment methods that avoid such problems.

SUMMARY OF THE INVENTION

Systems, kits, methods and computer program products for medical treatments and fee provisioning for the same are provided.

In one embodiment a medical treatment system comprises an electronic controller having a microprocessor and a microprocessor-readable data storage medium with microprocessor-executable instructions for applying specific medical treatment control parameters to a medical treatment apparatus operatively coupled to the electronic controller. A data reader is operatively coupled to the microprocessor of the controller and receives instructions from a physical ancillary data storage medium coupled to or packaged with an ancillary treatment apparatus configured for use with the electronic medical treatment apparatus, wherein the instructions for are at least some of the instructions for applying the specific medical treatment control parameters. A display is also operatively coupled to the microprocessor of the controller to provide a visual confirmation that the electronic medical treatment apparatus is activated for use with the ancillary treatment apparatus.

In one embodiment the electronic medical treatment apparatus is an acoustic pressure wave device including, but not limited to a shock wave device. Non-limiting and exemplary shock wave devices include an electrohydraulic shock wave device (or spark gap), electromagnetic shock wave device, piezoelectric shock wave device. In some embodiment a ballistic applicator may be used to provide acoustic pressure waves. In embodiments of the system including an acoustic pressure wave device, the ancillary treatment apparatuses include one or more of sleeve, pad, sterility barrier, reflector, lens and an applicator head.

In embodiments of the invention, a medical treatment system further includes a physical data input device, including but not limited to a keyboard, mouse, electronic tablet, electronic measuring instruments, photographic or video data capturing instruments and like interfaces for data input to a controller. The controller in various embodiments may process the input data to provide a visual output to the display to inform a user as to what ancillary treatment apparatus and accompanying physical ancillary storage medium is appropriate from among different ancillary treatment apparatuses for use in a particular medical treatment. In particular embodiments, the data input to the data input device may include wound measurements, body area volumes, body part identification, a medical condition identification and the like.

In one embodiment, a medical kit includes one or more ancillary treatment apparatuses and at least one treatment information storage device having information indicative of a medical treatment. In exemplary embodiments, the treatment information storage device may include information for security provisioning, indicative of medical treatment settings and/or for tracking inventory of the kit and/or the device with which the kit is used to provide medical treatment. In various embodiments, the treatment information storage device is a radio frequency identification ("RFID") card, a dongle or a barcode.

In embodiments, the type and number of ancillary treatment apparatus are indicative of the medical treatment, and the cost of the medical treatment is electronically stored in the treatment information storage device. Accordingly, a supplier of the medical treatment kit may obtain payment for a medical treatment upon the sale of the kit. Medical treatment kits may be sold to purchasers at different prices, based on the specific treatments that can be performed using them, based on the geographical region in which they will be used or based on any other parameters related to medical provisioning. The purchasers may be the patients receiving the medical treatment and/or medical personnel or facilities administering the medical treatment. Accordingly, the type and number of the ancillary treatment apparatus may be consistent with the medical treatment information stored on the treatment information storage device.

In various embodiments, the ancillary treatment apparatus may be a coupling gel or material, a drape and/or a sleeve. The ancillary treatment apparatus may be any component or material configured to provide connectivity between the medical treatment apparatus and the patient. The coupling material may allow transmission of the shock wave with minimal attenuation. In some embodiments, the ancillary treatment apparatus may be any component or material for providing a sterile barrier between a medical treatment apparatus and a patient. Accordingly, the ancillary treatment apparatus may be designed to be disposable for one time use to avoid cross contamination between patients. In some embodiments, the ancillary treatment apparatus may be provided to be reusable.

In some embodiments, the ancillary treatment apparatus and the treatment information storage device may be scanned before being placed in the kit together. This method of matching the ancillary treatment apparatus with the information storage device may be used to ensure that the components are compatible with one another and/or are appropriate for the medical treatment for which the kit is being sold. If the components are not compatible, an indication of such may be provided to a kit assembler. If detection of incompatibility was not made during assembly, the medical personnel may receive an indication that there is a problem in embodiments wherein the medical personnel has equipment for confirming the compatibility of the contents of the kit.

In another embodiment, a medical treatment system is provided. The medical treatment system may include a medical treatment kit, a controller for controlling a medical treatment and a medical treatment apparatus for providing the medical treatment. The controller may be configured to receive the information from the treatment information storage device and/or generate corresponding control information for performing the medical treatment. The controller may also be configured to provide security by authenticating itself and/or the medical treatment apparatus with the treatment information storage device; and/or generate information for identifying itself and/or the medical treatment apparatus to provide inventory tracking. The controller may also be configured to: generate information for fee provisioning after a medical treatment has ended; and/or tabulate medical treatment data after a treatment has ended for recordkeeping purposes.

The medical treatment in one embodiment may be the administration of shock waves for human and/or animal afflictions. The shock waves may be applied extracorporeally and produced using any methods for providing shock waves including, but not limited to, electrohydraulic, electromagnetic, piezoelectric and/or explosion detonation methods. Each treatment may include a certain number of shocks, at a certain energy level and frequency indicative of the treatment settings stored in the treatment information storage device. Based on these treatment settings, the cost of the kit, which may be the cost of the medical treatment, may be determined and paid at the time of purchase of the kit. Alternately, payment for the medical treatment may be provided after the treatment has ended through fee provisioning systems, methods and/or computer program products.

In various embodiments, methods for providing medical treatment are provided. An exemplary method may include authenticating the controller and/or medical treatment apparatus by the region in which the controller and/or medical treatment apparatus are located; enabling the controller to operate if authentication is successful; operating the controller to perform a medical treatment via the medical treatment apparatus; and tabulating data indicative of the medical treatment for recordkeeping and for fee provisioning.

In another embodiment, a computer program product for fee provisioning is provided. The computer program product includes a computer-readable medium having computer-readable program code stored on the computer-readable medium and configured to be accessed by a processor to cause the processor to: identify a plurality of treatment settings indicative of a medical treatment; assign a value to an identified treatment setting; identify a type of ancillary treatment apparatus to be used in providing the medical treatment; assign a value to an identified type of ancillary treatment apparatus; and determine a fee corresponding to the medical treatment. In some embodiments, fee provisioning may identify a fee based only on the medical treatment settings provided during a medical treatment.

BRIEF DESCRIPTION OF THE DRAWINGS

These and other features and aspects of exemplary embodiments of the invention will become evident when the following detailed description is read with reference to the accompanying drawings wherein:

FIG. 15 is a table of treatment information of a medical treatment system according to an embodiment of the invention;

DETAILED DESCRIPTION OF THE INVENTION

Embodiments of the invention will be described with reference to the accompanying drawings and figures wherein like numbers represent like elements throughout. Further, it is to be understood that the phraseology and terminology used herein is for the purpose of description and should not be regarded as limiting. The use of "including", "comprising", or "having" and variations thereof herein is meant to encompass the items listed thereafter and equivalents thereof as well as additional items. The terms "mounted", "connected", and "coupled" are used broadly and encompass both direct and indirect mounting, connecting and coupling. Further, "connected" and "coupled" are not restricted to physical or mechanical connections or couplings.

Figure 1:
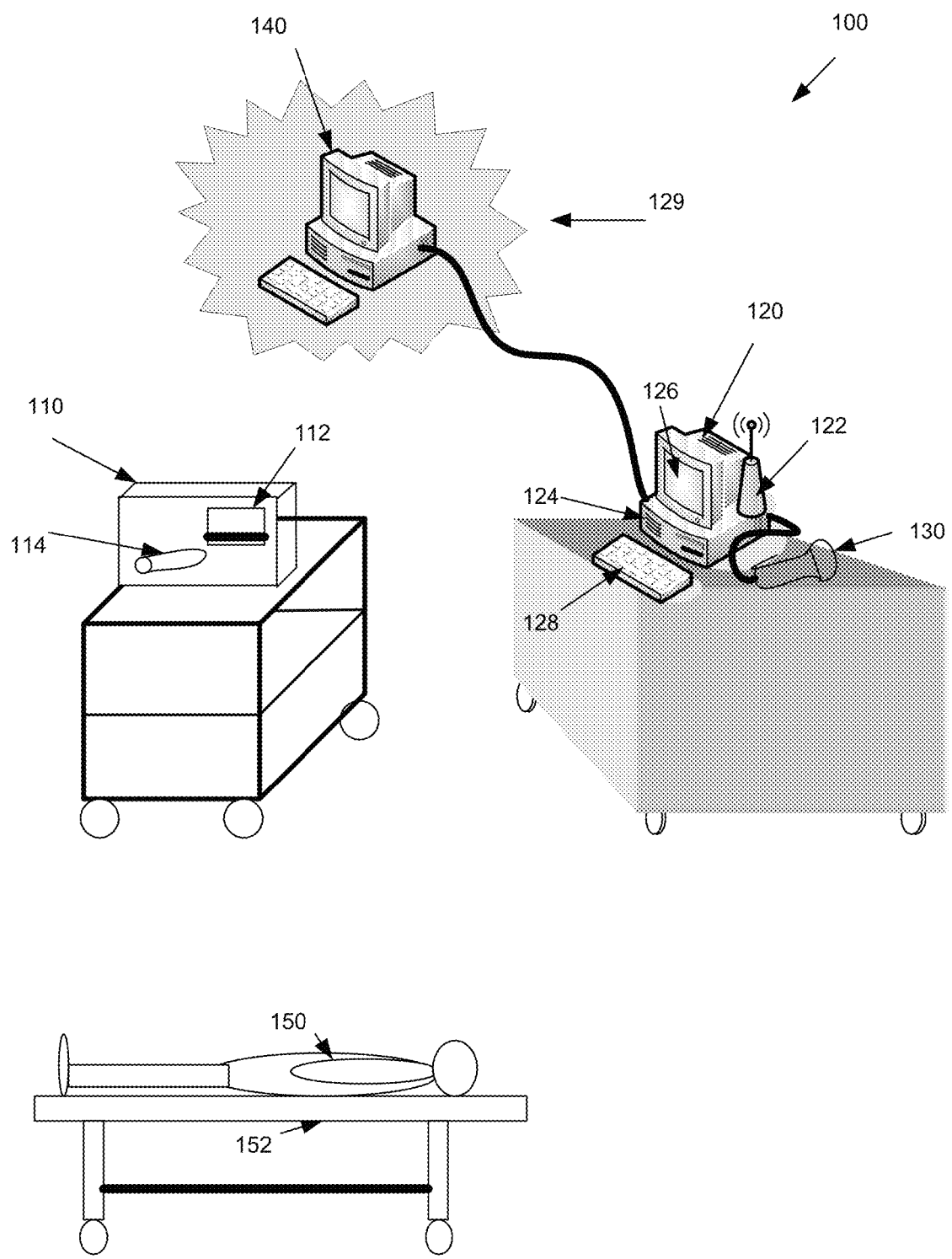
FIG. 1 is a schematic illustration of a medical treatment system according to an embodiment of the invention.

FIG. 1 is an illustration of a medical treatment system according to an embodiment of the invention. As shown in FIG. 1, the medical treatment system 100 includes a medical treatment kit 110, a controller 120 and a medical treatment apparatus 130.

Controller 120 is provided in embodiments as an electronic controller including a specially programmed medical system computer, including a microprocessor and microprocessor-readable storage medium of the controller 120. The microprocessor-readable storage medium of the controller 120 includes in embodiments microprocessor-executable instructions for applying specific medical treatment control parameters to a medical treatment apparatus 130. In embodiments, medical treatment apparatus is electronic and operatively connected to an electronic controller 120 for receipt of the parameters and control of the treatment.

In some embodiments, the medical treatment system 100 also includes a fee provisioning controller 140, which may be located proximate to the controller 120 or at any location within a communication network 129. In some embodiments, the medical treatment system 100 also includes a patient 150 and a support structure 152 on which the patient 150 may be positioned while receiving a medical treatment.

In some embodiments, one or more components of medical treatment system 100 may be located in a medical treatment facility (not shown) and communicatively coupled to any other component of the medical treatment system 100. The one or more components may be coupled by optical, electrical, wireline or wireless media. In some embodiments, the components may be coupled by such mechanisms via a universal serial bus ("USB") or an RS 232 port. In some embodiments, various components of medical treatment system 100 may be located proximate to or remote from other components, and the communication network 129 may be provided for transmitting and receiving information to and from one or more components.

Medical treatment kit 110 may be a disposable and/or consumable. Accordingly, the kit 110 may be a one-time use kit or a reusable kit. The medical treatment kit 110 may be provided for the treatment of any human or animal soft, semi-soft and/or hard tissue, including, but not limited to, bone, cartilage, muscle, tendons, ligaments, joints and their capsules, internal organs, glands, skin, blood vessels, lymphatic vessels, open and closed wounds, nerves or otherwise. The same kits 110 can be used to treat body fluids as synovial fluid, blood, etc. Additionally, medical treatment kit 110 may be used for any suitable medical procedure including, but not limited to, those medical procedures directed to human or animal treatment related to wound care, laminitis, osteoarthritis, plantar fasciitis, lateral epicondylitis, ulcers, pressure sores, skin conditions, cellulite, organ cancers, enlargement or cancers of glands, cardiological and vascular afflictions, urinary and sexual diseases, bone grafting or the like.

In the embodiment of the invention shown in FIG. 1, the medical treatment kit 110 includes a treatment information storage device 112 and an ancillary treatment apparatus 114. The treatment information storage device 112 is a physical ancillary data storage medium such as coupled to or packaged with, including coupled to a kit container, an ancillary treatment apparatus 114. The treatment information storage device 112 may have information stored thereon, as a for performing one or more functions related to providing medical treatment on the patient 150. In embodiments, the treatment information storage device 112 is used with controller 120 and includes at least some of the instructions, readable by a microprocessor of the controller, for applying a specific medical treatment control parameters for a medical treatment system. By way of example, but not limitation, treatment information storage device 112 may be an RFID tag, label or chip, memory stick, smart card, credit card, barcode, floppy disk, cd-rom, digital versatile disk ("DVD") or any device configured to store information and from which information may be read. The ancillary treatment apparatus 114 may be used in conjunction with the medical treatment apparatus 130 to enhance the medical procedure performed on the patient 150.

In various embodiments, the treatment information storage device 112 may perform payment provisioning, security, inventory tracking or medical treatment setting provisioning or any combination of these functions. In various embodiments, the treatment information storage device 112 may perform: storage of medical treatment settings corresponding to a medical treatment to be provided to the patient 150; enabling the controller 120 to be powered on; providing security by authenticating the controller 120 and/or the medical treatment apparatus 130; providing the cost of the medical treatment kit 110 to be charged to a purchaser of the kit 110; providing information for fee provisioning; and/or tracking inventory of the medical treatment kit 110, the ancillary treatment apparatus 114, the controller 120 and/or the medical treatment apparatus 130.

By providing the cost of the medical treatment kit 110 to be charged to a purchaser of the medical treatment kit 110, a purchaser may pay for a medical treatment in advance of receiving the medical treatment. The price for the medical treatment kit 110 may be the price for the medical treatment for which the kit 110 is provided. Accordingly, the cost of the kit 110 may increase and decrease according to the cost of the medical treatment. For example, the cost of a medical treatment for treating a large wound may be greater than that for treating a small wound. Accordingly, a kit 110 for treating the large wound may be a higher price than a kit 110 for treating the small wound. Accordingly, in these embodiments, the cost of the kit 110 is the cost of the medical treatment and may not be related to the cost of the ancillary treatment apparatus 114 and/or the type or technology required to create the treatment information storage device 112. The treatment information storage device 112 may be read at the beginning or end of the treatment as well as during the treatment in various embodiments.

In another embodiment, treatment information storage device 112 may be an RFID device. In various embodiments, the RFID device may be a tag, label or chip and may include passive, active or semi-passive technology. In some embodiments, the RFID device may include RFID chipless technology or electronic product code technology. Chipless RFID devices may allow for discrete identification of RFID tags without an integrated circuit, thereby allowing tags to be printed directly onto the surface of the kit 110 at lower costs than traditional tags. In one embodiment, treatment information storage device 112 may be a passive tag that requires no electrical supply for powering the tag. In one embodiment, the passive tag may be the Hitachi μ-chip. The tag may be inside of a medical treatment kit 110 or it can be a label placed on the outside of the kit 110. In another embodiment, the treatment information storage device 112 may be a passive RFID tag incorporating electronic product code technology. In various embodiments, the treatment information storage device 112 may be a polymer tag such as that manufactured by PolyIC, which is located in Germany, or that is manufactured by Phillips, which is located in the Netherlands.

In various embodiments, an RFID device may communicate according to the International Standards Organization ("ISO") 14443 and/or the International Electrotechnical Commission ("IEC") 18000-6 standards. The RFID device may communicate up to a distance of 10 cm (i.e., 4 inches) in accordance with ISO 14443. The RFID device may be included in a smart label governed by ISO 15693. In one embodiment, the RFID device is a 13.567 MHz device.

Referring back to FIG. 1, in some embodiments, security information that may be encrypted or unencrypted may be stored in treatment information storage device 112. The information may be read to authenticate medical treatment apparatus 130 and/or controller 120. The authentication may ensure compatibility between the apparatus 130 and/or the controller 120 and/or the ancillary treatment apparatus 114. Additionally, the information may be used to determine whether the controller 120 is authorized to be used in the geographical region in which the controller 120 is located.

In each embodiment, if the components are authenticated, treatment information storage device 112 transmits treatment settings information to the controller 120 thereby allowing the medical treatment to be performed. If authentication fails, treatment information storage device 112 operates in such a fashion so as to not allow for the medical treatment to be performed. In one embodiment, the treatment information storage device 112 may prevent the controller 120 from operating.

In one embodiment, authentication is performed as follows. The information stored on the treatment information storage device 112 may act as a password that is transmitted to the controller 120. The password may be encrypted to prevent the password from being pirated and improperly enabling the controller 120 to be turned on. If the controller 120 matches the correct password then authentication is successful and the medical treatment is allowed. If the password is not matched, then the medical treatment is not allowed. Such may be performed by not transmitting the treatment data stored on the treatment information storage device 112 to the controller 120 so the controller 120 cannot perform the treatment or by maintaining the controller 120 in an "off" mode. The controller 120 may be maintained in the off mode, for example, by maintaining a switch in the off mode or by moving an internal switch to the off mode. Accordingly, access to the controller 120 may be denied and/or the controller 120 may be maintained in an off position or in a state otherwise unable to perform a medical treatment if authentication is not successful.

In another embodiment, information may be input from an input device 128 that may be used to determine an appropriate medical treatment kit 110 for treatment of a patient 150 is stored on the controller 120 before use of the treatment information storage device 112. The input device 128 may include, but is not limited to, a keyboard, mouse, human interface device, image or video capture devices, temperature sensors, measuring instruments and the like. The information may be a specific body part medical condition, physical and anatomical measurements of a treatment area, information indicative of the type of treatment (e.g., hard tissue, soft tissue) and/or the type of treatment (e.g., non-ablative, which does not kill tissue, or ablative, which kills tissue, stimulation, healing or any other type of medical treatment that may be performed using the controller 120 and medical treatment apparatus 130). The medical treatment necessary to address the physical and anatomical measurements and/or provide the type of desired treatment may be determined by the controller 120.

After storing this information in the controller 120, the controller 120 may identify a type of kit 110 appropriate for the medical treatment.

In another embodiment, the medical treatment system 100 includes a physical data input device 128 operatively coupled to the controller 120, and wherein the controller 120 includes a microprocessor-readable data storage medium including microprocessor-readable instructions for visually confirming on the display 126 that information for a treatment area of a body received from the physical data input device 128 is compatible with treatment by the electronic medical treatment apparatus 130 according to the instructions contained on the physical ancillary data storage medium 112.

In another embodiment, the medical treatment system 100, such as where the medical treatment apparatus 130 is an acoustic pressure wave device, includes a physical data input device 128 operatively coupled to the controller 120, and wherein the controller 120 includes a microprocessor-readable data storage medium including microprocessor-readable instructions for visually confirming on a display 126 that a body part identification or medical condition received from the physical data input device 128 is compatible with treatment by the electronic medical treatment apparatus 130 according to the instructions contained on the physical ancillary data storage medium 112.

In a further embodiment, the medical treatment system 100, such as where the medical treatment apparatus 130 is an acoustic pressure wave device, includes a physical data input device 128 operatively coupled to the controller 120, and wherein the controller 120 includes a microprocessor-readable data storage medium having microprocessor-executable instructions for displaying that the ancillary treatment apparatus 114 should be selected from among a plurality of available ancillary treatment apparatuses 114 based on medical treatment data received from the physical input device 128.

In some embodiments, a kit identified may be in accordance with a course of treatment utilizing different kits during the treatment regimen. The different kits may include respective ancillary physical storage medium with instructions for treatment parameters to be applied from the controller to the medical treatment apparatus at the particular stage of treatment or status of the condition. Information regarding that status of the condition, such as wound measurements, healing characteristics, and the like, may be input to controller 120 from input device 128, for determination of a kit in the treatment regimen or the kits may include progressive predetermined treatment settings for the expected course of treatment. As exemplary non-limiting embodiments, an appropriate kit (as compared to a previous or a subsequent use kit) may include instructions to the controller to increase or decrease intensity of a parameter, change dosage and the like.

In one embodiment, wound treatment may be identified as desired for the patient 150. In this embodiment, the kit 110 may be a wound kit. Because wounds differ in size, type and appropriate treatment, the information stored in the controller 120 may be indicative of the type of kit 110 that should be provided to treat the wound. The length, width, diameter and/or depth of the wound may be provided to determine the appropriate kit 110, as well as treatment parameters for controller 120 to apply for the treatment.

The selected wound kit may be opened and the treatment information storage device 112 may be removed and scanned. In response to scanning the treatment information storage device 112, the treatment information storage device 112 may perform authentication to determine if the wound kit is appropriate for the wound. If the wound kit is appropriate, the treatment settings stored in the treatment information storage device 112 may be transmitted to the controller 120. A wound kit may be determined to be appropriate based on treatment settings and/or treatment parameters. For example, treatment parameters may include an appropriate type for the controller 120, an appropriate type for the medical treatment apparatus 130 and an authorized geographical region in which the controller 120 and/or medical treatment apparatus 130 may be sold and/or used. For example, certain controllers 120 located in certain geographical regions may be authorized to operate only with certain medical treatment kits 110. Accordingly, controlling whether the controller 120 can operate may prevent the usage of kits 110 bought at a first, low price in a first region and used in a second region wherein the kit 110 would be sold at a higher price. In some embodiments, a Global Positioning System (GPS) receiver, wireless triangulation controller, Internet domain addresses and like location technologies may be used with the controller to determine a geographical region and associated geographical-based setting.

In other embodiments, the authentication ensures that the controller 120 is not used in regions wherein the government of the region has not authorized the controller 120 to be used. Accordingly, a controller 120 used in an inappropriate region may not be enabled to operate because the treatment information storage device 112 may only authenticate controllers 120 that it recognizes as authorized to be used in a certain region.

In alternative embodiments, a specific measurement of a desired volume of a body area to be treated with acoustic pressure waves may be input to controller 120 to set appropriate parameters for such volume as well as determination of an appropriate kit 110 for such treatment. A density measurement of the target body tissue or part may also be input to controller 120 for determination of appropriate treatment parameters and kit 110. Further, in other embodiments, the particular body part and/or medical condition may be input to controller 120 to set appropriate parameters for treatment of the body part and/or condition and to determine the appropriate kit 110 for such treatment.

Authentication may reduce the problem of erroneous selection of medical treatment kits 110, controllers 120 and parameters or any other device in the system. Such authentication may also increase the probability of effective treatment by reducing the probability of selecting primary and supplemental apparatus that reduce the effectiveness of one another.

Additionally, determining the identity of the devices and ensuring that the proper devices are being used reduces the likelihood of unsafe treatment. For example, the likelihood of unsafe dosages of energy and/or an unsafe number of shocks being applied to a patient 150 may be reduced because the treatment settings may be programmed into the treatment information storage device 112.

By way of example, in medical treatments for human or animal wound care, treatment settings for devices 112 may differ based on the area of the wound. Thus, in different embodiments of the invention, the different medical treatment kits may have treatment information storage devices 112 with different pre-programmed treatment settings created for kits 110 directed to treating wound areas that are small, medium, large, X-large, XX-large or XXX-large.

In various embodiments, treatment information storage device 112 may store information for facilitating security for medical treatment kit 110 to ensure that medical treatment kit 110 has not been tampered with in any regard.

In some embodiments, treatment information storage device 112 may be configured with a mechanism or information that may be used to track inventory of medical treatment kits 110, perform inventory control functions, reduce theft, facilitate fee provisioning, facilitate insurance coding, facilitate provisioning of payments for medical treatments in advance of receiving the medical treatments, provide security provisioning to enable the controller 120 to operate or the like, as described above.

In one embodiment, the treatment information storage device 112 may be used to facilitate provisioning of payment for a medical treatment. In this embodiment, based on the information from a treatment information storage device 112, the controller 120 may be programmed with medical treatment settings and perform the treatment. In response to the treatment ending, the treatment settings used may be recorded in a tabular form and then transmitted to fee provisioning controller 140, which uses the data to calculate the payment for the treatment. The fee provisioning controller 140 may also use the data to perform insurance coding. The information may also generate data about what was done for the treatment and store the data in the controller 120 for a period of time (or for a selected number of future treatments). The tabulated data may also be used to determine whether the controller 120 is malfunctioning and reimburse the patient 150 if it is determined that there is malfunctioning or acts of God preventing proper operation of the controller 120 or apparatus 130. The fee provisioning controller 140 can also be used to store data for tracking the treatment of the patient 150.

After ending treatment, the log of the treatment may be stored inside the controller 120. The way that treatment is ended may be determined and evaluated. When treatment is ended by a shut off of the controller 120, a hard shut off or a soft shut off may occur. As used herein, the term "hard shut off" shall mean, a shut off of the controller 120 after a power failure, due to a faulty controller 120 or apparatus 130, after switching the main switch directly to turn off the controller 120 device or by unplugging the controller 120 from the power source. As used herein, the term "soft shut off" shall mean shut off of the controller 120 after a proper shut off by pushing the stand-by button or activating another mechanism for properly stopping the operation of the controller 120 and/or the medical treatment apparatus 130 after a medical treatment has ended.

When a hard shut off occurs, the patient 150 may be reimbursed for the treatment being performed. In cases wherein the log of the treatment is indicative of the controller 120 being shut down in a manner so as to avoid detection that a medical treatment has been performed, the controller 120 may be stopped and not started again until authorization by a third-party having the power to authorize the controller 120 to be able to be started again. The log of treatment may be indicative of attempts to avoid detection when there have been a selected number of consecutive hard shuts. For example, after three hard shuts, the controller 120 may be shut down until an authorized third-party starts the controller 120 again. The pattern of attempting to avoid detection may differ from that disclosed above.

In one embodiment, treatment information storage device 112 includes a barcode that can be used to transfer medical treatment settings. The barcode can also be used to provide the cost of the kit 110 for payment of a medical treatment in advance of receiving the medical treatment. In some embodiments, the barcode may also be used to track inventory of the kit 110.

Treatment information storage device 112 may be disposable and/or consumable and thereby provided only for a single-use medical treatment or be reusable and thereby provided for more than one treatment for a patient 150. Treatment information storage device 112 may be able to be recharged or have information stored thereon updated, increased or decreased in value. The treatment settings or values thereof may be added, increased, decreased or otherwise changed upon medical treatment system 100 or treatment information storage device 112 receiving value such as monetary value. Accordingly, treatment information storage device 112 may be updated with a value in a manner similar to that for telephone calling cards to which value may be added. Systems and methods for adding value or changing values may be performed by any of the well-known ways of adding value to a mechanism. Alternately, adding or changing values may be performed at the manufacturer of the described system of components or via internet or electronic connection using protected encryption systems.

Information stored on the treatment information storage device 112 may be stored in any manner suitable for facilitating a medical treatment. For example, in various embodiments, the information may be stored as random access memory, read only memory, flash memory or the like.

Medical treatment kit 110 also includes an ancillary treatment apparatus 114. Ancillary treatment apparatus 114 may be disposable and/or consumable. Ancillary treatment apparatus 114 may be any device designed to be used during a medical procedure. In various embodiments, ancillary treatment apparatus 114 may be a device configured to generate and/or emit one or more acoustic pressure waves, including shock waves, or can be the interface used between the medical treatment apparatus 130 and the patient 150. In various embodiments, medical treatment apparatus 130 may be an acoustic pressure wave device. The applicator may generate in various embodiments shock waves through electromechanical, electromagnetic, explosive detonation, electrohydraulic, piezoelectric (crystals, thin films or fibers) or any other suitable methods for generating shock waves. The shock waves may be focused or non-focused and may be non-sinusoidal, sharp and high pressure waves having a relatively short distance in time between the crest and trough of the wave. In some embodiments, the shock waves are sinusoidal, ultrasonic focused or non-focused waves or microwaves.

In one embodiment, ancillary treatment apparatus 114 provides enhanced cleanliness for the medical treatment. In this embodiment, the apparatus 114 may be sterile and disposable for one-time use. In this regard, ancillary treatment apparatus 114 may be a covering mechanism disposed to cover at least a portion of a surface of the medical treatment apparatus 130. In this regard, the covering mechanism may be disposed to be positioned between medical treatment apparatus 130 and patient 150 during a medical procedure to reduce the likelihood of cross-contamination between different patients that receive treatment from the same medical treatment apparatus 130. In various embodiments, ancillary treatment apparatus 114 may, include, but is not limited to, a sleeve, sterility barrier, disposable or re-usable head, membrane, ellipsoidal, spherical or parabolic (or a combination thereof) reflector or disposable reflectors with variable focus, pad solution, pad with integrated antibiotics or other pharmaceuticals, drug delivery devices, gels and the like.

Ancillary treatment apparatus 114 may be disposed to be coupled to medical treatment apparatus 130 such that ancillary treatment apparatus 114 pivots, or tilts, at a location at which ancillary treatment apparatus 114 is coupled to medical treatment apparatus 130. Ancillary treatment apparatus 114 may be disposed to be coupled to medical treatment apparatus 130 such that ancillary treatment apparatus 114 moves along a first axis and/or a second axis before, after or while pivoting/tilting. The pivoting/tilting may be three dimensional. The first axis and second axis may be perpendicular to or positioned at any suitable angle to the surface of patient 150 to which treatment is provided. Accordingly, movement may be vertical towards and away from patient 150 or front to back or side to side relative to a surface of the patient 150. For medical treatments including shock wave application, vertical movement towards and away from patient 150 may provide different depths of shock wave penetration for different vertical heights of medical treatment apparatus 130 relative to patient 150. For medical treatments such as those including cardiac treatments wherein treatment area within patient 150 is constrained or patient 150 may not tolerate vertical movement toward or away from patient 150 or front to back or side to side treatment, pivoting/tilting movement may be provided to provide proper medical treatment. Fee provisioning may be performed based on the type of treatment provided. For example, a fee may be assessed for the different types of treatments wherein pivoting/tilting may be a greater or a lesser fee than vertical movement toward and away from the patient.

In some embodiments, ancillary treatment apparatus 114 is one of several different applicators that may be used for treatment.

In some embodiments, ancillary treatment apparatus 114 provides enhanced acoustic coupling between medical treatment apparatus 130 and patient 150 with minimal attenuation of shock waves that may be emitted from medical treatment apparatus 130. In this regard, ancillary treatment apparatus 114 may be a gel pad that may be disposed to be positioned between the surface of medical treatment apparatus 130 and patient 150 or coupling gel that may be disposed to be applied to patient 150. Other kinds of gel pads or coupling gel can be used to attenuate the shocks and reduce the harm or injury of the shock waves in selected areas during, before and/or after the treatment area.

In some embodiments, ancillary treatment apparatus 114 may be any mechanism that aids in reducing cross-contamination between patients using the medical treatment apparatus 130.

Controller 120 includes reader 122, computer 124, display 126 and user input apparatus 128. Each of the components may include hardware, software or a combination of hardware and software configured to perform one or more functions associated with providing medical treatment and/or fee provisioning for medical treatment. In various embodiments, the controller 120 may be operative: to receive medical treatment settings corresponding to a medical treatment to be provided to a patient 150; to be powered on; to be authenticated; and/or to process information for fee provisioning. The controller 120 may also be configured to tabulate data and/or keep a record of the type of treatment provided including, but not limited to, the number of shock waves provided.

Additionally, a data reader 122, a computer 124 including a microprocessor and a microprocessor-readable storage medium, display 126 and user input apparatus 128 may be communicatively coupled to one or more of each other through any of the media described above.

Reader 122 may be any mechanism configured to read information from treatment information storage device 112, including, but not limited to, optical character recognition ("OCR") reader, barcode reader, RFID reader or the like. Reader 122 may read the information by any of several well-known methods, including, but not limited to, RFID scanning or optical character recognition.

In some embodiments, reader 122 may be an RFID reader and/or a scanner that may be coupled to controller 120 and a power supply (not shown). This RFID reader and/or scanner may be able to activate an RFID passive tag and read the information embedded in it.

Reader 122 may read the RFID device when the RFID device is within a selected proximity to reader 122. In some embodiments, the selected proximity is a few centimeters in compliance with the ISO 14443 or ISO15693 standard. Reader 122 and the RFID tag may be configured to communicate at specific frequencies and for different distance ranges. In one embodiment, the RFID reader may be RFID reader and writer model no. ID CPR.Mo2 manufactured by Feig Electronic and may be used in conjunction with an RS-232 interface.

Controller 120 also includes computer 124 and, in some embodiments, may also include display 126 and user input apparatus 128. In some embodiments, controller 120 and components therein may include electromechanical components, which are activated by sophisticated software and hardware components.

Computer 124 includes software, hardware or a combination of both software and hardware configured to receive and process information indicative of one or more treatment settings read from treatment information storage device 112 by reader 122. In one embodiment, computer 124 processes the read information and generates control information configured to be received by and control the functionality of medical treatment apparatus 130. Accordingly, medical treatment apparatus 130 may receive the control information and be controlled to operate in accordance with one or more of the treatment settings stored on treatment information storage device 112. In some embodiments, controller 120 downloads the treatment settings from treatment information storage device 112.

Figure 19:
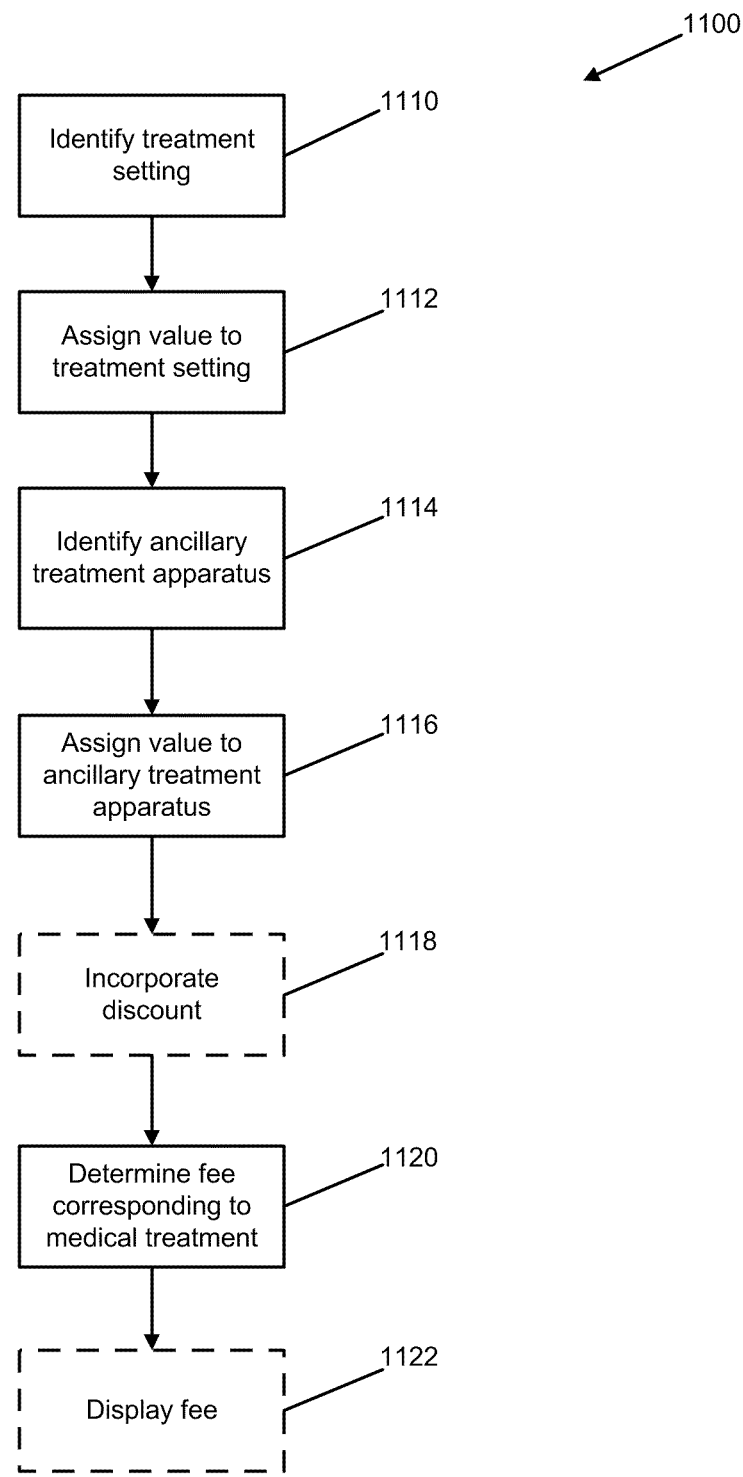
FIG. 19 is a flow diagram illustrating a method of operation of a medical system according to an embodiment of the invention.

In some embodiments, computer 124 may also be configured to provide one or more functions associated with fee provisioning. In this regard, computer 124 may perform a method for determining a fee associated with one or more medical treatments or an entire medical procedure that includes the one or more medical treatments. Referring to FIG. 19, the method may be method 1100 or another suitable method for fee provisioning for medical treatments.

Referring again to FIG. 1, in various embodiments, computer 124 may be configured to enable the controller 120 to receive medical treatment settings corresponding to a medical treatment to be provided to a patient 150, be powered on, be authenticated, and/or process information for later-generating invoices for payments for the medical treatment provided.

User input apparatus 128 includes software, hardware or a combination of both software and hardware configured to receive inputs initiated by a user and translate the received inputs to signals disposed to be interpreted by one or more of computer 124, display 126 or reader 122. In one embodiment, the received inputs are translated into signals configured to cause reader 122 to read and/or scan the information of treatment information storage device 112. In one embodiment, the received inputs are translated into signals configured to cause a mechanism to write to a memory of treatment information storage device 112. The mechanism may thereby update one or more of the treatment settings. In one example, after the patient 150 has received a medical treatment, the mechanism may write to the memory of the treatment information storage device 112 to decrease the number of remaining treatments by one. In another example, after the patient 150 provides a form of payment to medical personnel, the mechanism may write to the memory of treatment information storage device 112 to replenish the number of shocks that the patient 150 may receive using treatment information storage device 112. To prevent re-usage, in another embodiment the treatment information storage device 112 may be destroyed after the information contained on it is transferred to the controller 120.

Display 126 includes software, hardware or a combination of both software and hardware configured to receive and format for visual display, image information indicative of one or more treatment settings read by reader 122. The visual display may be graphical, pictoral, text or otherwise. In one embodiment, the display 126 may be able to display the information at different angles. In one embodiment, display 126 may be a graphical user interface ("GUI"). The GUI may be a touchscreen GUI or a GUI configured to receive signals from inputs received at user input apparatus 128.

In one embodiment, display 126 displays instructions readable by medical personnel for guiding the medical personnel through a procedure. In another embodiment, instructions may be provided for performing one or more of initializing controller 120 or apparatus 130; loading treatment settings and loading information indicative of the type of medical treatment kit 110; or starting a new treatment. Display 126 may output the treatment area, frequency, energy, penetration depth, applicator type, selected dose, date and/or time of treatment. The display 126 may also display an image of the treatment area.

Medical treatment apparatus 130 includes software, hardware or a combination of both software and hardware configured to provide a medical treatment. The apparatus 130 may also include security authentication components driven by the hardware and software included in either the treatment information storage device 112 or the controller 120.

In some embodiments, medical treatment apparatus 130 may be a device configured to generate and emit one or more shock waves by any number of methods including, but not limited to, electrohydraulic, piezoelectric (e.g., crystal, thin films or fibers), electromagnetic methods and/or explosion methods that can generate planar, radial, focused or non-focused waves. In one embodiment, apparatus 130 is a spark gap generator configured to generate shock waves. In various embodiments, medical treatment apparatus 130 is any mechanism configured to provide medical treatment. The medical treatment may be shock wave therapy. In some embodiments, medical treatment apparatus 130 is a mechanism configured to provide shock wave treatment to the body.

In various embodiments, medical treatment apparatus 130 may be a device configured to provide an x-ray of the patient 150 or ultrasound scanning or computed tomography of the patient or any other medical treatment or scanning procedure that may be provided to a patient by an automated device. Medical treatment apparatus 130 may be designed to be used in conjunction with ancillary treatment apparatus 114. In one embodiment, ancillary treatment apparatus 114 may be mechanically, electrically, magnetically or merely physically coupled to medical treatment apparatus 130. In some embodiments, a first end of medical treatment apparatus 130 proximate to the patient 150 may be disposed to be covered in whole or in part by ancillary treatment apparatus 114 thereby reducing the risk of cross-contamination between patients using medical treatment apparatus 130.

In various embodiments, controller 120, medical treatment apparatus 130 and/or ancillary treatment apparatus 114 may be configured with various treatment settings and/or operate according to specific treatment settings.

With reference to FIG. 1, in some embodiments, medical treatment apparatus 130 may include a shock wave housing including or configured to operate with a changeable ancillary treatment apparatus 114 for applying shock waves. In another example, medical treatment apparatus 130 may be mountable to the support structure 152 on which patient 150 may be disposed while receiving treatment. The medical treatment apparatus 130 may include a number of different electrodes for different treatments.

The medical treatment apparatus 130 may operate in response to the controller 120 receiving treatment settings regarding voltage, energy, frequency, number and/or angle of shock waves to be applied to the patient 150. In one embodiment, a voltage of 10-20 kV may be used to generate the shock waves applied to the patient 150 at a frequency of 1-20 Hz. Shock wave application may be started and/or re-started as necessary until treatment is completed. A voltage of 5-30 kV may be used to generate the shock waves applied to patient 150 at a frequency of 1-8 Hz and shock wave application may be started and/or re-started as necessary until treatment is completed. Ancillary treatment apparatus 114 may be a sterility barrier or one of several different applicators that may be used with the medical treatment apparatus 130.

Medical treatment apparatus 130 may dictate the Input/Output ("I/O") information for user input apparatus 128 and display 126. In one embodiment, the user input apparatus may include an on/off mechanism, a mechanism for receiving treatment settings regarding energy, frequency of shock waves, a preselected dose of shock waves, the number of shocks per area, a position parameter for automatic positioning of the apparatus 130 and/or an editing tool such as an electronic pencil disposed to cooperate with a display 126 configured as a touchscreen for manually editing an image of a treatment area. A wound size may be defined with the editing tool. The editing tool may be used to identify the coordinates of a wound and such coordinates may be sent as electronic signals to medical treatment apparatus 130, which may automatically calculate the treatment area. In some embodiments, existing x-ray or ultrasound pictures may be imported into controller 120 and may be shown on display 126. Accordingly, medical personnel may be able to view an internal area of patient 150 to aid in positioning medical treatment apparatus 130.

In another example, a computer, such as a laptop and the like, (not shown) can be coupled to the medical treatment apparatus 130, to control the way the information is received from the controller 120. Medical treatment apparatus 130 may dictate the input and output information that may be displayed on the laptop or on any other suitable device configured to communicate with the laptop. For example, in one embodiment, medical treatment apparatus 130 is a device that can be connected to a laptop and used by a patient or an in-home caregiver. User input apparatus 128 may include an on/off mechanism for turning the laptop on and off, respectively.

The fee provisioning controller 140 may be any mechanism configured to process received information indicative of a medical treatment and generate a value for the medical treatment. In various embodiments, the fee provisioning controller 140 may be a database configured with medical treatment settings and values. The fee provisioning controller 140 may correlate the received information with the medical treatment settings and the values may be the cost of the medical treatment based on the medical treatment settings. Accordingly, the received information may be indicative of the information stored on the treatment information storage device 114. For example, in one embodiment, a monetary fee indicative of a cost that the patient 150 is billed or must pay at the time of the treatment is determined. The determination may be made based on the number and frequency of shock waves and the energy level of the medical treatment apparatus 130 provided during the medical treatment. In this embodiment of the medical treatment system 100, the monetary fee is the payment for the medical treatment. The payment is to be collected from the patient 150 at a time after the purchase of the medical treatment kit 110 and after the conclusion of the medical treatment.

Fee provisioning controller 140 may be communicatively coupled to one or more of the controller 120, medical treatment apparatus 130 or treatment information storage device 112. In some embodiments, the fee provisioning controller 140 may be located at a geographical location that is remote from the medical treatment system 100. For example, as shown, the fee provisioning controller 140 may be located at any address within a communication network 129.

In another embodiment of a medical treatment system (not shown), a treatment information storage device may be used without association with any medical treatment kit. Treatment information storage device may be used in a fashion similar to a telephone calling card and may be programmed to have selected values for treatment settings.

For example, a treatment information storage device may have a limited number of shock waves programmed thereon, based on the money value paid when the treatment information storage device was purchased. In some embodiments, these treatment information storage devices may be offered to the patient pre-loaded with a certain number of shock waves (e.g., 2500, 5000, 10000) at different costs. In some embodiments, the higher the number of shock waves loaded on the device, the higher the cost of the treatment information storage device. The number of shock waves consumed during a treatment can be deducted from an initial number of shock waves purchased on the device, and treatment may be repeated until all of the shock waves have been used. In some embodiments, after all of the shock waves have been applied and no shock waves remain, the treatment information storage device can be updated and uploaded. This credit card approach can be used for different medical treatments. Accordingly, a treatment information storage device may be independent of a medical treatment kit and therefore not associated with a certain medical treatment kit or medical treatment for a certain kind of illness. In this way, this approach allows flexibility for the patient to choose treatment setting values based on medical treatment needs (which may include more than one medical treatment need) and keep costs low instead of paying in advance for a large number of shocks, which might not be financially feasible for some patients.

Additionally, combinations of one or more of the aforementioned embodiments can be created and other treatment information storage devices might be used to create modalities to financially charge, program treatment settings, provide security and/or keep a record of treatments.

In some embodiments, a medical treatment kit (not shown) may be provided for the administration of pharmaceuticals and/or drugs to humans or animals. By way of example, pharmaceuticals may be those for the treatment of human or animal wounds, hard and soft tissue diseases, cardiac, orthopedic or neurological diseases and/or for provisioning of vaccines, anesthetic agents, antibiotics, contraceptives, antiparasitic drugs or the like. In various embodiments, substances that can be pushed inside the human body, tissues or cells using a medical treatment apparatus such as a shock wave device.

In some embodiments, the medical treatment kit may include a treatment information storage device, such as that having electronic product code technology, and an ancillary treatment apparatus such as a dispenser disposed to contain pharmaceuticals. For example, the medical treatment kit may include a syringe having a label or tag formatted with electronic product code technology. The label may have information stored therein identifying the pharmaceutical, a proper medical treatment for which the pharmaceutical may be used and proper dosage information for the medical treatment. By scanning this information and transferring it to a controller, the patient can receive the right treatment. In another embodiment the information from the syringe and/or medical container can contain programming data for the treatment setting that can be transferred to the controller before the treatment.

In response to a reader of a controller reading the information stored in the label, the controller may determine whether the pharmaceutical is appropriate for the patient and/or for the medical treatment. In some embodiments, the controller may cross-reference information (e.g., age, allergies, etc.) in a medical history or profile of the patient to whom the pharmaceutical is to be provided to determine whether the pharmaceutical is compatible with the patient or with the treatment that the patient is scheduled to receive.

The medical history and/or profile may be previously-stored in an information repository accessible by the controller at the location of the controller or accessible over a network at a location remote to the controller. Alternately, the medical history and/or profile may be input into a system accessible by the controller or read by a provider (e.g., doctor or nurse) of the pharmaceutical at the time of the medical treatment. For example, the medical history and/or profile may be stored on a CD, floppy disk, on paper in a patients file or otherwise. The electronic device can be customized for each patient, by having part of its memory allocated to do the customization when a series of treatment starts for the respective patient. The rest of the memory is used for treatment settings, number of shocks consumed or available, etc.

Accordingly, the kit may be used to reduce the incidents of providing erroneous pharmaceuticals or dosages of such to patients. Such may be especially useful with pharmaceuticals that vary significantly in strength but for which the packaging of the different strengths is not significantly different and therefore may not be noticed by the provider of the pharmaceutical.

For example, if the profile indicates that the patient is an infant, and the information that is read from the label indicates that the pharmaceutical is for an adult or is otherwise too strong for the infant receiving the medical treatment, the controller may perform steps to provide an alert such that the pharmaceutical is not provided to the infant.

FIGS. 2, 3, 4, 5, 6 and 7 depict controllers and treatment information storage devices of the medical treatment system of FIG. 1 according to embodiments of the invention.

Figure 2:
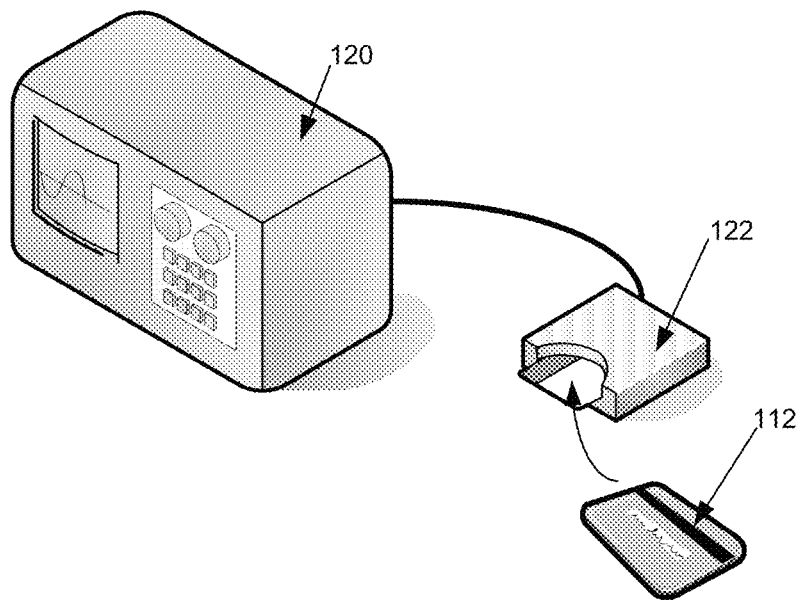
FIG. 2 is a schematic illustration of an electronic controller, ancillary physical data storage medium and wired data reader of a medical treatment system according to an embodiment of the invention.

With reference to FIG. 2, controller 120 includes hardware positioned to read device 112 upon insertion into reader 122. In one embodiment, device 112 is inserted into reader 122 and remains during treatment.

Figure 3:
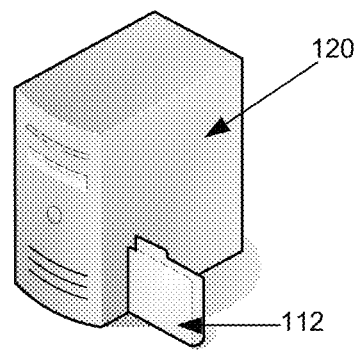
FIG. 3 is a schematic illustration of an electronic controller, ancillary physical data storage medium connected by a dongle in a medical treatment system according to an embodiment of the invention.

With reference to FIG. 3, controller 120 is configured to receive treatment information storage device 112, which may be any type of dongle, including, but not limited to, a memory stick. The dongle may be connected to a USB or RS232 port (not shown).

The dongle may couple to the controller 120 and may be used to authenticate and enable the controller 120 to operate when the dongle is coupled to the controller 120. Accordingly, the dongle may be used as a security device.

In one embodiment, information is stored as read only memory on a treatment information storage device 112 that is reusable for multiple medical treatment sessions. In this regard, a patient may provide treatment information storage device 112 to a medical provider at each treatment session. The information stored on treatment information storage device 112 may be accessed to determine and provide the aspects of the medical treatment session stored thereon. In one embodiment, each session may be associated with one or more different aspects of treatment as the patient goes through a series of treatments to complete the entire medical procedure. The information stored on the treatment information storage device 112 may be indicative of the aspects of each of the numerous sessions included in the entire medical procedure and may thus dictate the type of treatment to be provided at each session.

In another embodiment, the device 112 may be able to communicate with the controller 120 and can retrieve information on the treatment and any other notes introduced by the physician during treatment. In this way the device 112 may become personalized and can be used by patient to track how many treatments are left, what was done in the previous treatments, how much the costs were for the previous treatments, etc. These devices 112 may be given to the patients and scanned with the controller 120 before each treatment to access the history of the previous treatments and how many treatments are left, etc. After the whole treatment is finished, if the device 112 is reusable, the patient may return the device 112 to a location associated with a manufacturer of the device 112 and have the device 112 reprogrammed for a new series of treatments.

Figure 4:
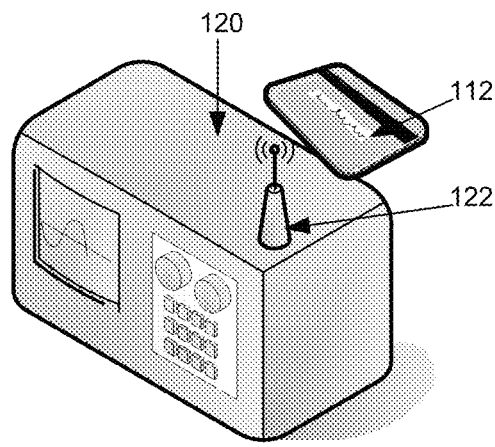
FIG. 4 is a schematic illustration of an electronic controller, ancillary physical RFID data storage medium and RFID data reader of a medical treatment system according to an embodiment of the invention.

With reference to FIG. 4, controller 120 is configured with an RFID scanning reader 122 on a surface of controller 120 for scanning treatment information storage device 112. Treatment information storage device 112 may be an RFID tag in proximity of the scanning reader 122.

Figure 5:
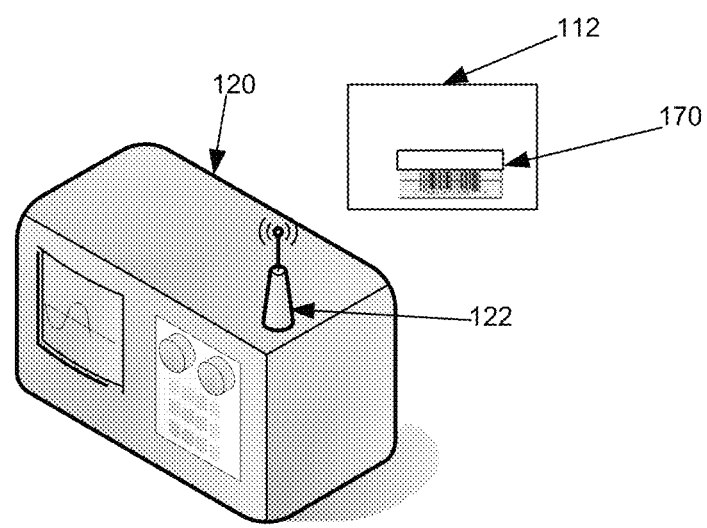
FIG. 5 is a schematic illustration of an electronic controller, ancillary physical data storage medium in a label and RFID data reader of a medical treatment system according to an embodiment of the invention.

With reference to FIG. 5, controller 120 may also have reader 122 including antenna configured to activate a treatment information storage device 112. Treatment information storage device 112 may be an RFID device incorporated in a label 170 of a kit (not shown). In one embodiment, the treatment information storage device 112 may employ chipless RFID technology. Controller 120 may scan the activated RFID device 112.

Figure 6:
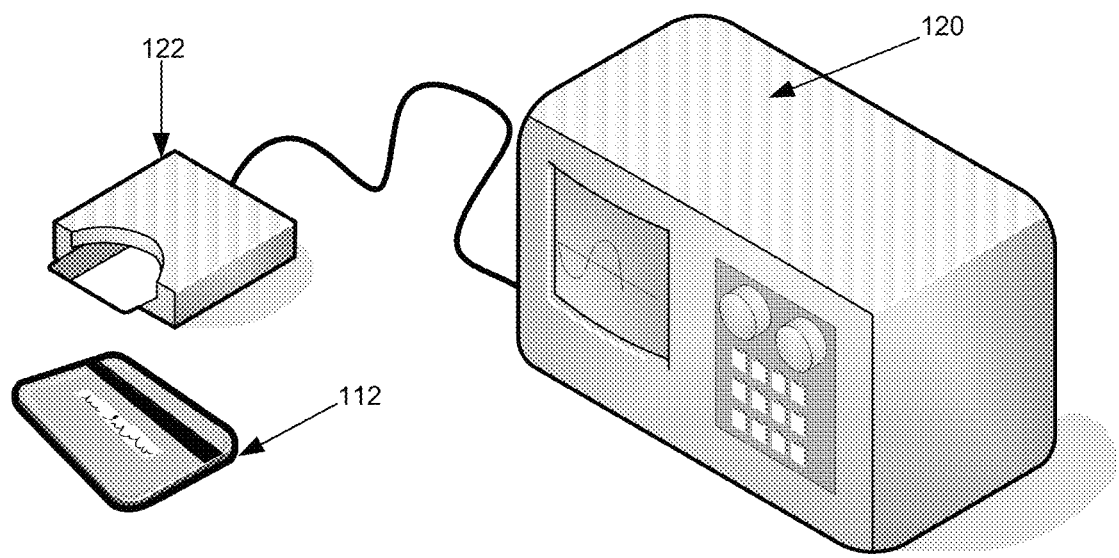
FIG. 6 is a schematic illustration of an electronic controller, ancillary physical data storage medium and magnetic card data reader of a medical treatment system according to an embodiment of the invention.

With reference to FIG. 6, controller 120 may include a magnetic card reader 122 configured to read a magnetic stripe of a treatment information storage device 112, similar to a credit card reader and swiping device that can be seen in retail shops.

Figure 7:
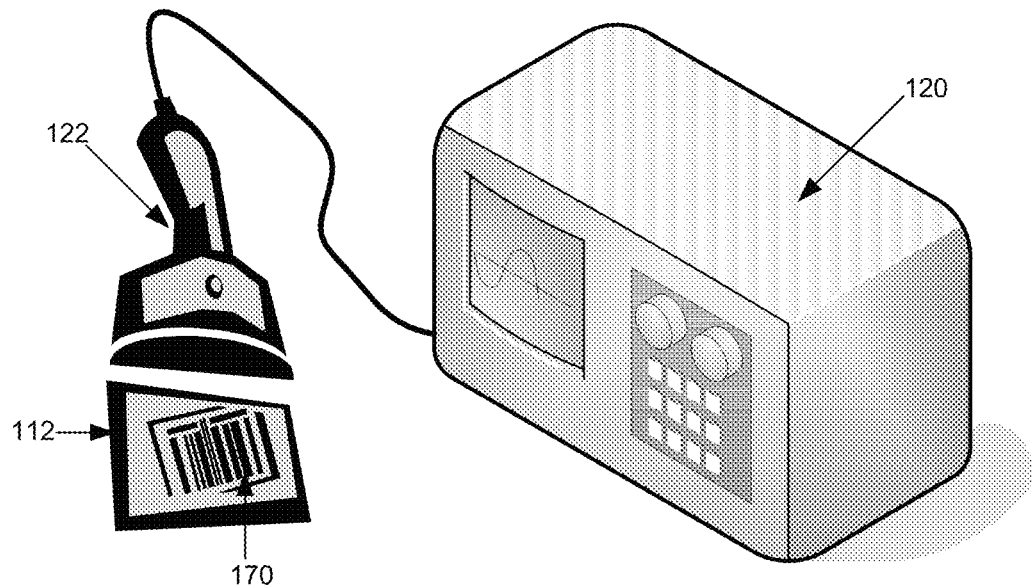
FIG. 7 is a schematic illustration of an electronic controller, ancillary treatment data storage medium with a bar code and bar code data reader of a medical treatment system according to an embodiment of the invention.

With reference to FIG. 7, controller 120 may include a barcode reader 122 configured to read a barcode of a treatment information storage device 112. Treatment information storage device 112 may be a barcode such as may be provided on a label 170 of a kit (not shown).

Figure 8:
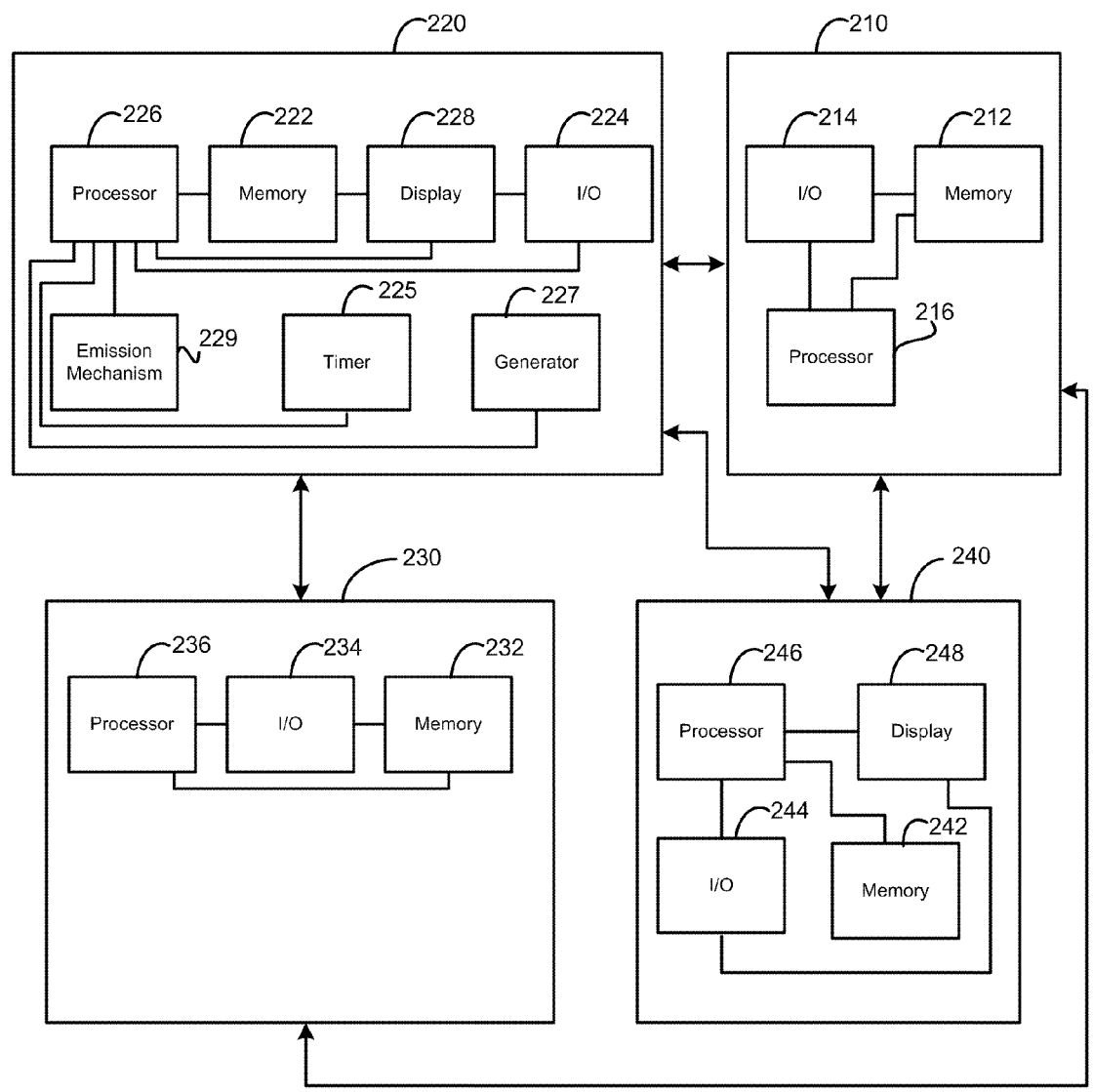
FIG. 8 is a relational block diagram of the medical treatment system according to an embodiment of the invention.

FIG. 8 is a block diagram of a medical treatment system according to an embodiment of the invention. The block diagram depicts a medical treatment kit subsystem 210, a controller subsystem 220, a medical treatment apparatus subsystem 230 and a fee provisioning subsystem 240. Medical treatment kit subsystem 210 includes a memory 212 and a kit I/O device 214. In some embodiments, kit subsystem 210 also includes a processor 216. Memory 212 may be any type of memory configured to maintain information regarding medical treatment and provide security via authentication of the controller subsystem 220 and/or the medical treatment apparatus subsystem 230. For example, memory 212 may contain information indicative of one or more treatment settings of a medical treatment. Kit I/O device 214 may be communicatively coupled to memory 212 and disposed to transmit from kit subsystem 210 the information indicative of the one or more treatment settings of a medical treatment. Kit I/O device 214 may also be configured to receive information such as updated information indicative of new treatment settings resultant from a completed medical treatment. In one embodiment, kit I/O device 214 may receive information indicating that a treatment has been administered and transmit the information to processor 216. The processor 216 may decrement by one a treatment setting indicative of the number of treatments allowed to a patient using the kit subsystem 210. The updated treatment setting may then be written on memory 212 for subsequent accessing and use during a next medical treatment.

Controller subsystem 220 includes a memory 222, a controller I/O device 224, a processor 226, emission mechanism 229, timer 225, generator 227, and, in some embodiments, controller display device 228. Memory 222 may be any type of memory configured to store downloaded information regarding one or more treatment settings. In one embodiment, controller I/O device 224 receives information indicative of one or more treatment settings from kit subsystem 210, processes the received information to generate a control signal for controlling treatment subsystem 230. The controller I/O device 224 may transmit the control information to treatment subsystem 230. Controller display device 228 may provide a visual display of graphics and/or text indicative of the one or more treatment settings, patient identity information, ancillary treatment apparatus selection, patient insurance information, treatment apparatus activation or the like. Additionally, in some embodiments, controller display device 228 may provide a visual display of current treatment. For example, display device 228 may provide an indicator of the amount of treatment remaining before, during or after a medical treatment. In another embodiment, device 228 may provide a display of one or more interior body regions being studied when treatment subsystem 230 includes an x-ray device that is utilized to x-ray a region of a patient.

In one embodiment, controller subsystem 220 processes information received in processor 226 and transmits the information received to generator 227 and timer 225. Generator 227 and timer 225 provide control information for generating a selected number of shock waves by utilizing a selected amount of energy as determined by the one or more treatment settings transmitted from kit subsystem 210. Generator 227 may include hardware or components for providing, via the treatment subsystem 230, one or more shock waves by electromechanical, electromagnetic, electrohydraulic, explosive detonation, or piezoelectric methods, which are well-known to those skilled in the art. Timer 225 provides timing for emitting the one or more generated shock waves at a selected frequency as dictated by the one or more treatment settings. The one or more shock waves are emitted in a manner controlled by the emission mechanism 229.

Treatment subsystem 230 includes a memory 232, a treatment I/O device 234 and a processor 236. In one embodiment, memory 232 may be any type of memory configured to store downloaded information regarding one or more treatment settings. In some embodiments, memory 232 is any type of memory configured to store control information indicative of the one or more treatment settings or control signals for controlling the operation of the treatment subsystem 230. Treatment subsystem 230 may receive control information from controller subsystem 220 and output shock waves or provide other medical treatment according to the control information resultant from processing in processor 226, emission mechanism 229, timer 225 or generator 227.

Fee provisioning subsystem 240 includes a fee provisioning memory 242, a fee provisioning I/O device 244, a fee provisioning processor 246 and fee provisioning display device 248. In one embodiment, memory 242 may be any type of memory configured to store information regarding one or more treatment settings, one or more ancillary treatment apparatus used during a medical treatment administered by treatment subsystem 230, and/or one or more medical treatments currently or previously performed. In one embodiment, I/O device 244 receives information indicative of one or more treatment settings, one or more ancillary treatment apparatus used during a medical treatment administered by treatment subsystem 230, and/or one or more medical treatments performed. Processor 246 processes the received information and determines a monetary fee indicative of the one or more treatment settings, one or more ancillary treatment apparatus used during a medical treatment administered by treatment subsystem 230, and/or one or more medical treatments performed.

Figure 9:
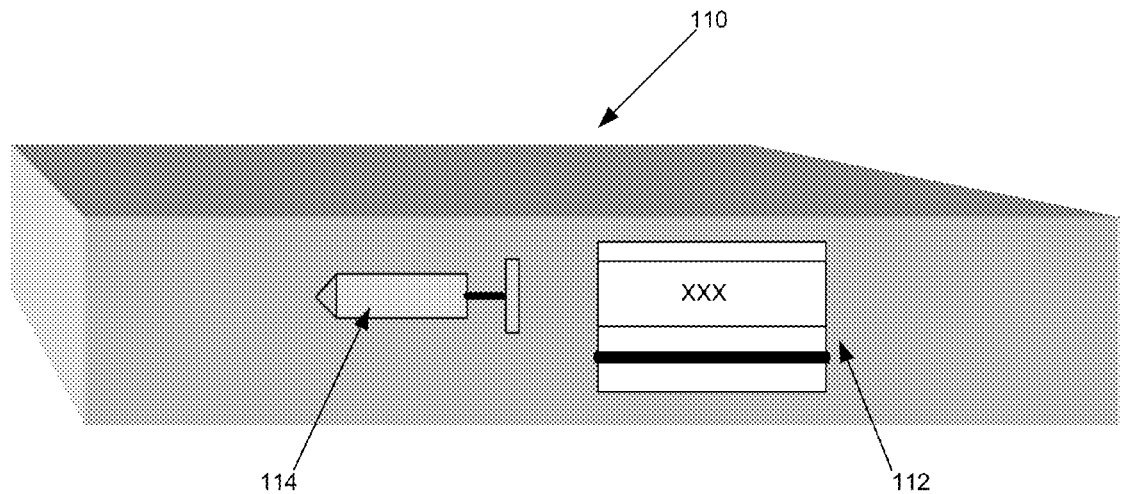
FIG. 9 is a schematic illustration of a treatment kit according to an embodiment of the invention.
Figure 10:
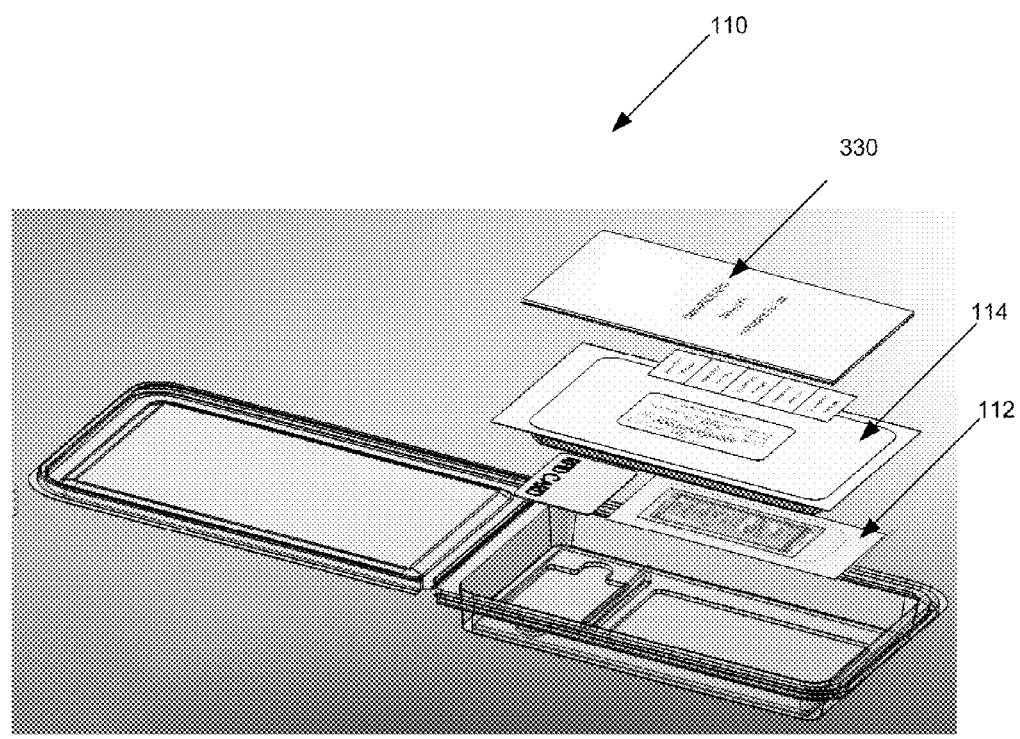
FIG. 10 is a perspective view from above of a treatment kit according to an embodiment of the invention.
Figure 11:
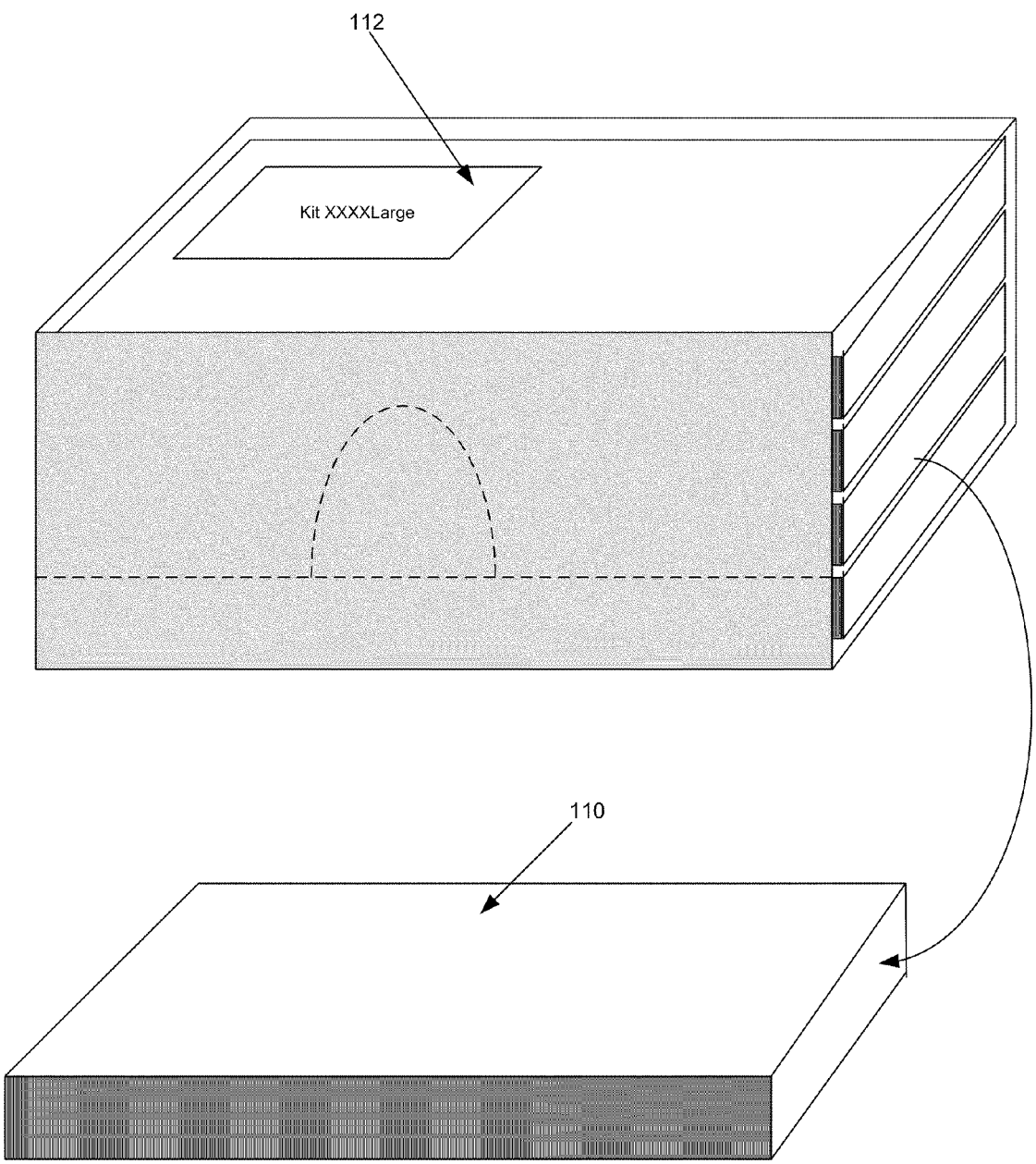
FIG. 11 is a schematic illustration of an individual treatment kit among a plurality of medical treatment kits according to an embodiment of the invention.
Figure 12:
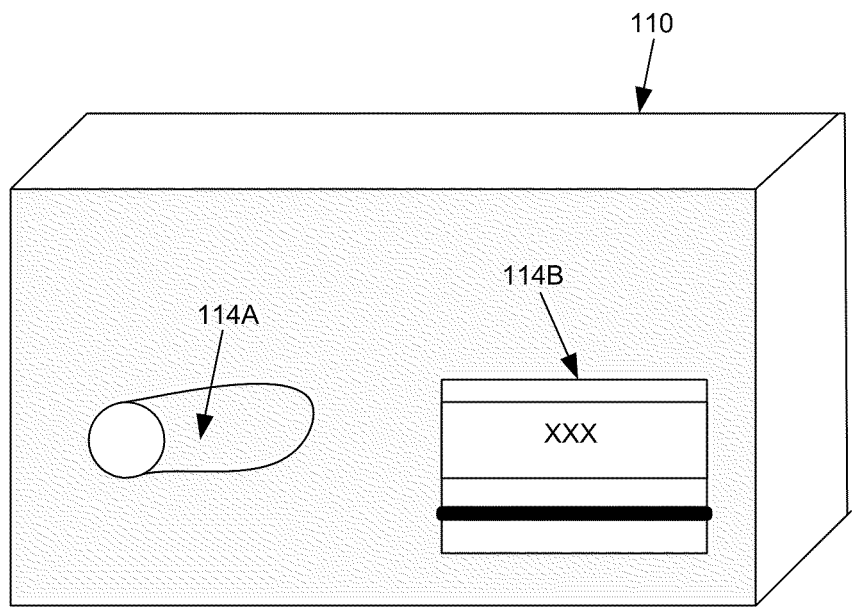
FIG. 12 is a schematic illustration of a treatment kit including two ancillary treatment apparatuses of a gel and a shock wave device sleeve in an embodiment of the invention.
Figure 13:
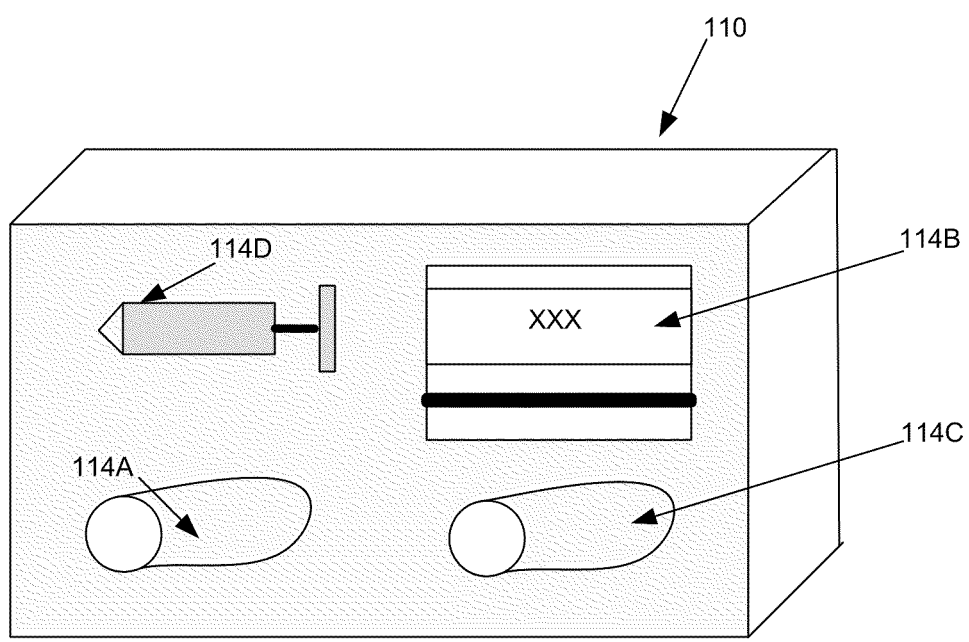
FIG. 13 is a schematic illustration of a treatment kit including four ancillary treatment apparatuses of two gels, a shock wave device sleeve and a gel applicator device in an embodiment of the invention.
Figure 14:
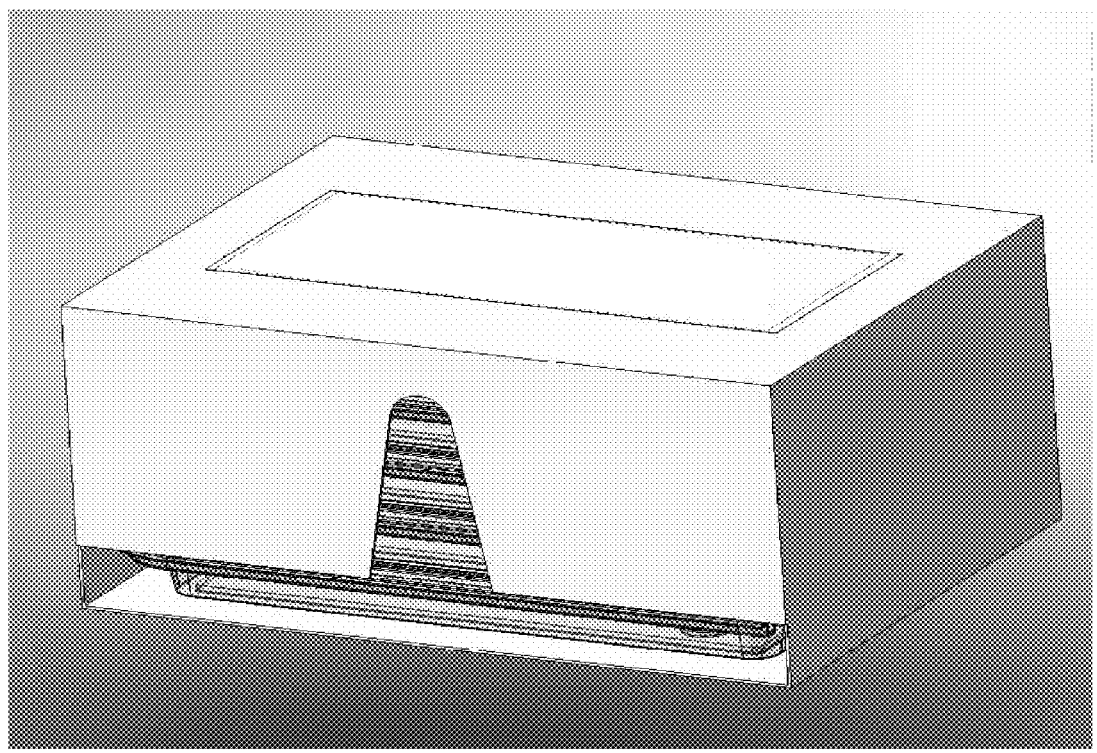
FIG. 14 is a perspective view of a dispenser carton having a plurality of medical treatments kits in an embodiment of the invention.

FIGS. 9, 10 and 11 depict medical treatment kits according to embodiments of the invention. FIGS. 12 and 13 also show views of medical treatment kits of the medical treatment system according to embodiments of the invention. FIG. 14 is a perspective view of a dispenser carton having a plurality of the medical treatments kits. FIGS. 9-13 illustrate various embodiments of kits with reference to ancillary treatment apparatus and treatment information storage devices, each of which may be designed as any of the embodiments described with reference to FIG. 1.

With reference to FIG. 9, kit 110 houses in one embodiment an ancillary treatment apparatus 114, such as a syringe or other dosage applicator, and treatment information storage device 112. With reference to FIG. 10, kit 110 houses an ancillary treatment apparatus 114 embodied as a sleeve that may be provided on a medical treatment apparatus (not shown), and also houses a treatment information storage device 112 that is an RFID card. The kit 110 also includes a label 330 identifying the manufacturer of the kit in some embodiments. In this embodiment, treatment information storage device 112 is a barcode label. In various embodiments, treatment information storage device 112 may be an RFID tag, label, chip or payment/credit card. Referring to FIG. 11, kit 110 includes an ancillary treatment apparatus (not shown) located on an interior of kit 110 and treatment information storage device 112 positioned on a label disposed to be viewed from the exterior of kit 110. In another embodiment, the label is positioned on the interior surface of kit 110 and kit 110 has a transparent housing providing viewing of the label from the outside of kit 110. Referring to FIG. 12, kit 110 houses two ancillary treatment apparatuses 114A and 114B. In the embodiment shown, kit 110 includes a sleeve 114B and coupling gel 114A. Referring to FIG. 13, kit 110 houses four ancillary treatment apparatuses 114A-114B. In the embodiment shown, kit 110 includes a sleeve 114B, two coupling gels, 114A and 114C and an applicator 114D. In other embodiments, the contents can be any parts used in charging for, providing or otherwise related to a medical treatment. In the embodiment shown, the applicator 114D is a disposable applicator. In kits 110, treatment information storage device (not shown) may be provided on the exterior surface of the respective kit or housed inside of the kit. In other embodiments, a treatment information storage device may be coupled to one of the ancillary treatment apparatuses or provided within the kit.

FIG. 14 is an illustration of a dispenser carton having a plurality of the medical treatments kits such as shown in one or more of FIGS. 9-13.

FIG. 15 is a diagram of treatment information of a medical treatment system according to embodiments of the invention. The treatment information may include treatment parameters and/or treatment settings. The treatment parameters may include any information indicative of an aspect of a medical procedure, including, but not limited to, the aspects of the treatment style applied to the patient and the equipment used to apply the medical procedure. The treatment settings may include, but are not limited to, electronic settings for configuring the controller 120 and/or the medical treatment apparatus 130 to operate to perform the medical treatment.

In one exemplary embodiment, the treatment parameters may include information indicative of: the number of treatments to provide to a patient 710, the length of time for each of the treatments 712, the total length of time for all treatments combined 714, a number of shock waves to apply to a patient in a treatment 716, a number of shock waves to apply to a patient over all treatments combined 718, a treatment area 724, a depth of penetration of shock waves into a patient 726, an ancillary treatment apparatus type 728 and/or an approved region 734 for the controller or medical treatment apparatus. The treatment settings may include a frequency at which to apply the shock waves to the patient 720, an energy setting and a controller type 732. In various embodiments, a medical treatment apparatus type 730 may be either a treatment parameter or a treatment setting.

With further reference to FIGS. 1 and 15, in some embodiments, the approved region setting 734 may be indicative of a region for which controller 120, medical treatment apparatus 130 and/or the medical treatment is approved. In this regard, only a controller 120, medical treatment apparatus 130 or medical treatment that has been approved in a particular region may be performed using the medical treatment kit 110. Accordingly, if controller 120 and/or medical treatment apparatus 130 is approved for use in the United States but not in Europe, medical treatment kit 110 may prevent the use of controller 120 and/or medical treatment apparatus 130 if medical treatment kit 110 is being presented outside of the United States. Additionally, one or more treatment settings may be designated to comply with requirements for a selected region. Accordingly, medical treatment kit 110 may allow the controller 120 to operate to provide medical treatment only in authorized regions of the world.

With reference to FIGS. 1 and 15, in one embodiment, treatment parameters are stored on the controller 120 and treatment settings are stored on the treatment information storage device 112. Accordingly, the treatment information storage device 112 may transfer the treatment settings to the controller 120 upon the treatment information storage device 112 being read. In some embodiments, the treatment settings may include the controller type 732 and/or the medical treatment apparatus type 730, and the treatment information storage device 112 may check the type of the controller 120 and/or the medical treatment apparatus 130 against the controller type 732 and/or medical treatment apparatus type 730 information. If the controller 120 and/or medical treatment apparatus 130 is determined to be the same type as the value of controller type 732 and/or the value of the medical treatment apparatus 130, the treatment information storage device 112 may allow the controller 120 to operate and/or control the medical treatment apparatus 130.

In another embodiment, one or more of the treatment parameters and one or more of the treatment settings are stored on the controller 120 in addition to the one or more treatment settings that may be stored on the treatment information storage device 112.

In one embodiment, the treatment information shown in FIG. 15 may be used as follows. A surface of a wound may be measured and the measurement information received by the controller 120. The controller 120 may receive the information in response to manual entry of the information by a medical personnel or by automatic entry of the information when the medical treatment system 100 includes apparatus for scanning and viewing portions of a the body of the patient 150. Based on the measurement information received by the controller 120, the controller 120 may identify an appropriate medical treatment kit 110 to be used for the medical treatment. The treatment information storage device 112 that is read by the controller 120 may be checked to determine if the treatment settings stored on the treatment information storage device 112 correspond to the type of medical treatment kit 110 that the controller 120 determines to be appropriate. The treatment settings may be indicative of the type of medical treatment and/or the wound size for which the medical treatment kit 110 is to be used. If the medical treatment kit 110 is appropriate, the controller 120 may receive the treatment settings and may be configured according to the treatment settings. When the treatment is completed, the controller 120 may add to a memory (not shown) in the controller 120, the measurement information. In one embodiment, the memory may be a table such as that shown in FIG. 15. Similar parameters by which the controller 120 operated may also be saved in the table. Accordingly, in some embodiments, treatment parameters applied during a medical treatment may be stored after the treatment is completed.

The aforementioned treatment parameters and treatment settings, along with their corresponding values, are merely exemplary and may include any other treatment parameters, treatment settings and values relevant for the treatment of any human or animal soft or hard tissue, including, but not limited to, an organ such as a liver, kidney, brain, heart, skin or any other organ, bone, teeth, gums, cartilage, muscle, tendons, ligaments, joints and their capsules, internal organs, glands, skin, blood vessels, lymphatic vessels, open and closed wounds, nerves or otherwise. Additionally, the tissue may be a part of the vascular, nervous, reproductive, urinary, lymph node, pituitary, skeletal or ocular systems. Additionally, the treatment parameters and/or treatment settings may describe aspects of treatment for any suitable medical procedure including, but not limited to, those medical procedures directed to human or animal treatment related to wound care, laminitis, osteoarthritis, plantar fasciitis, lateral epicondylitis, ulcers, pressure sores, cardiac, orthopedic or neurological treatment or bone grafting.

Figure 16:
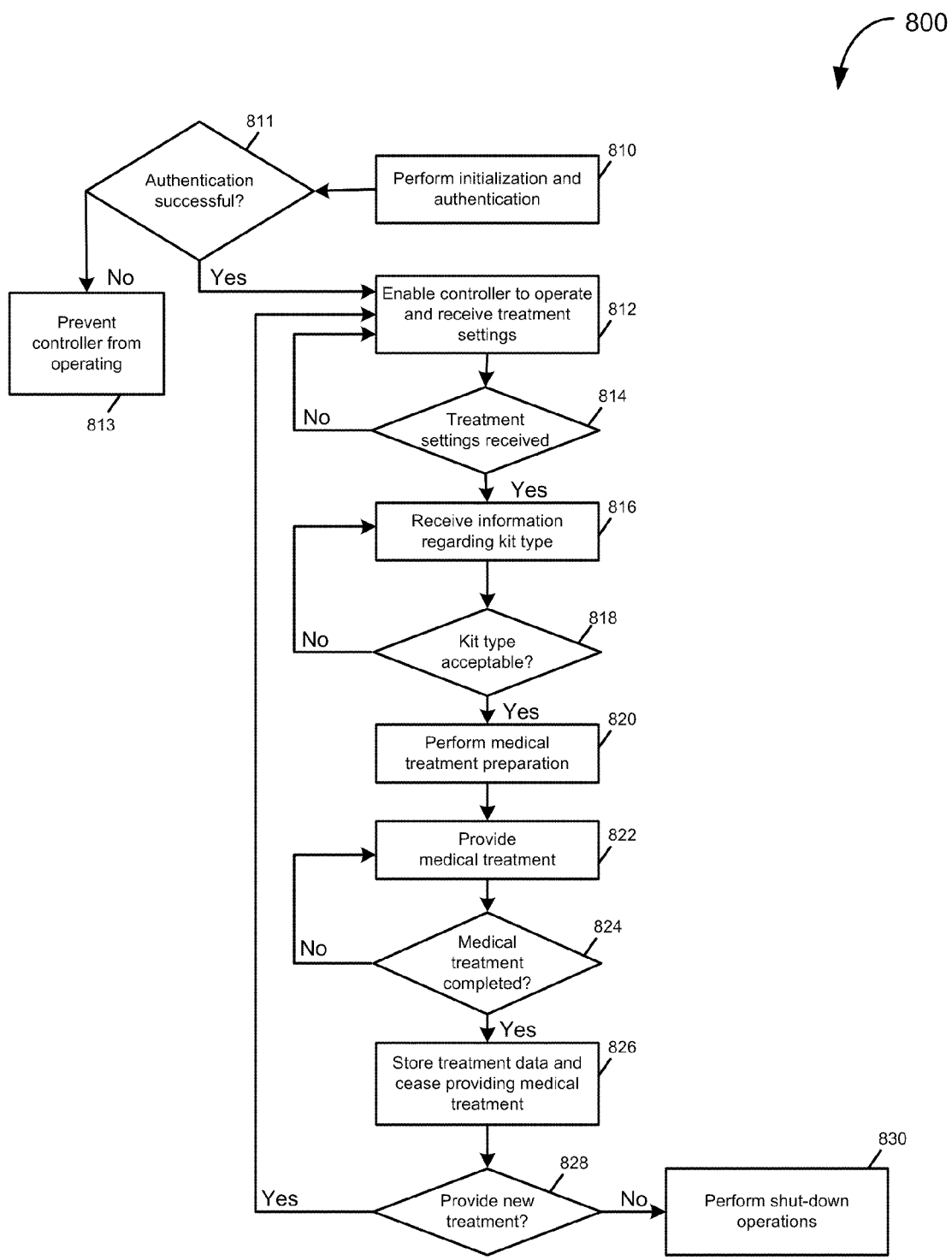
FIG. 16 is a flow diagram illustrating a method of operation of a medical system according to an embodiment of the invention.
Figure 17:
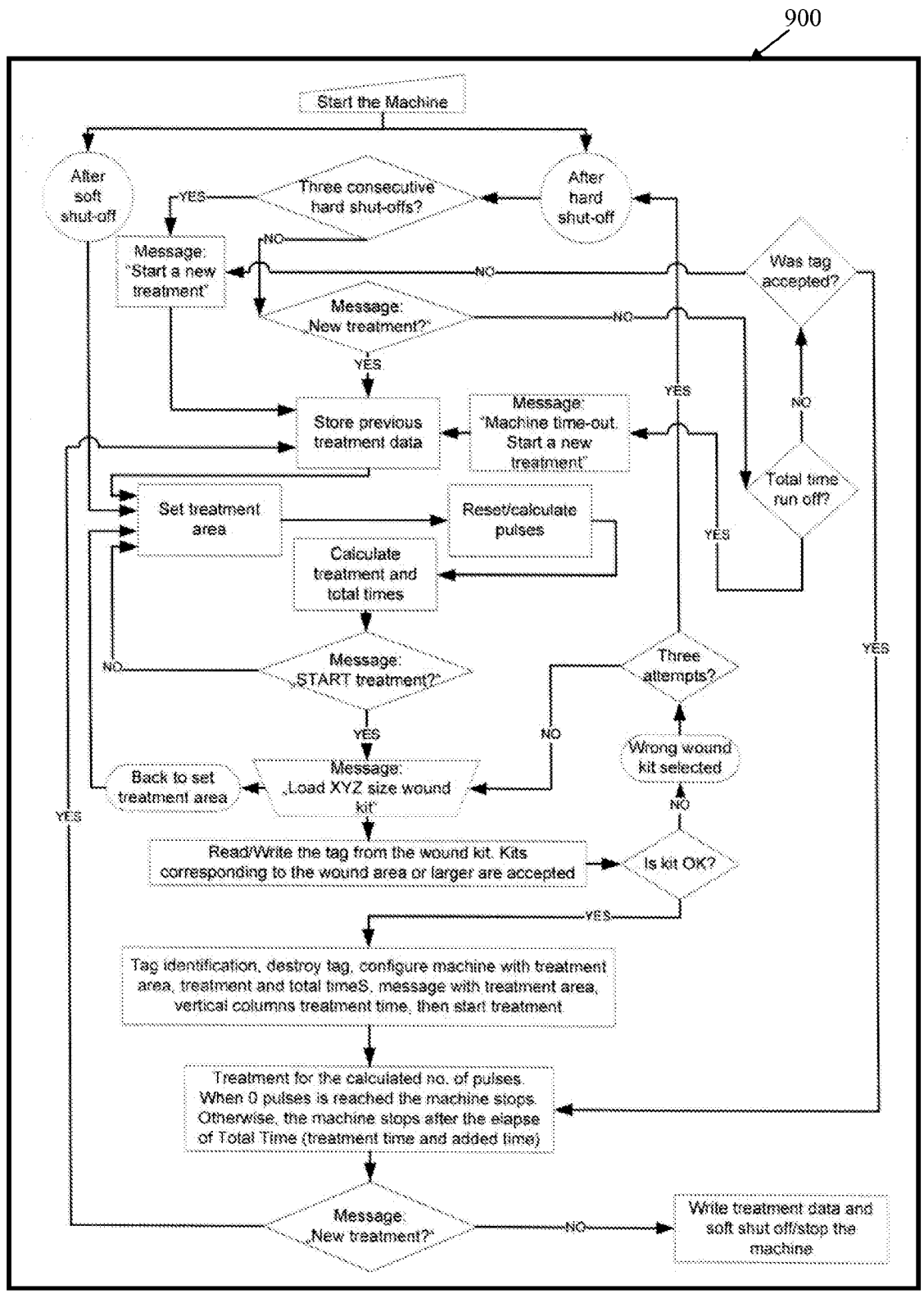
FIG. 17 is a flow diagram illustrating a method of operation of a medical system according to an embodiment of the invention.
Figure 18:
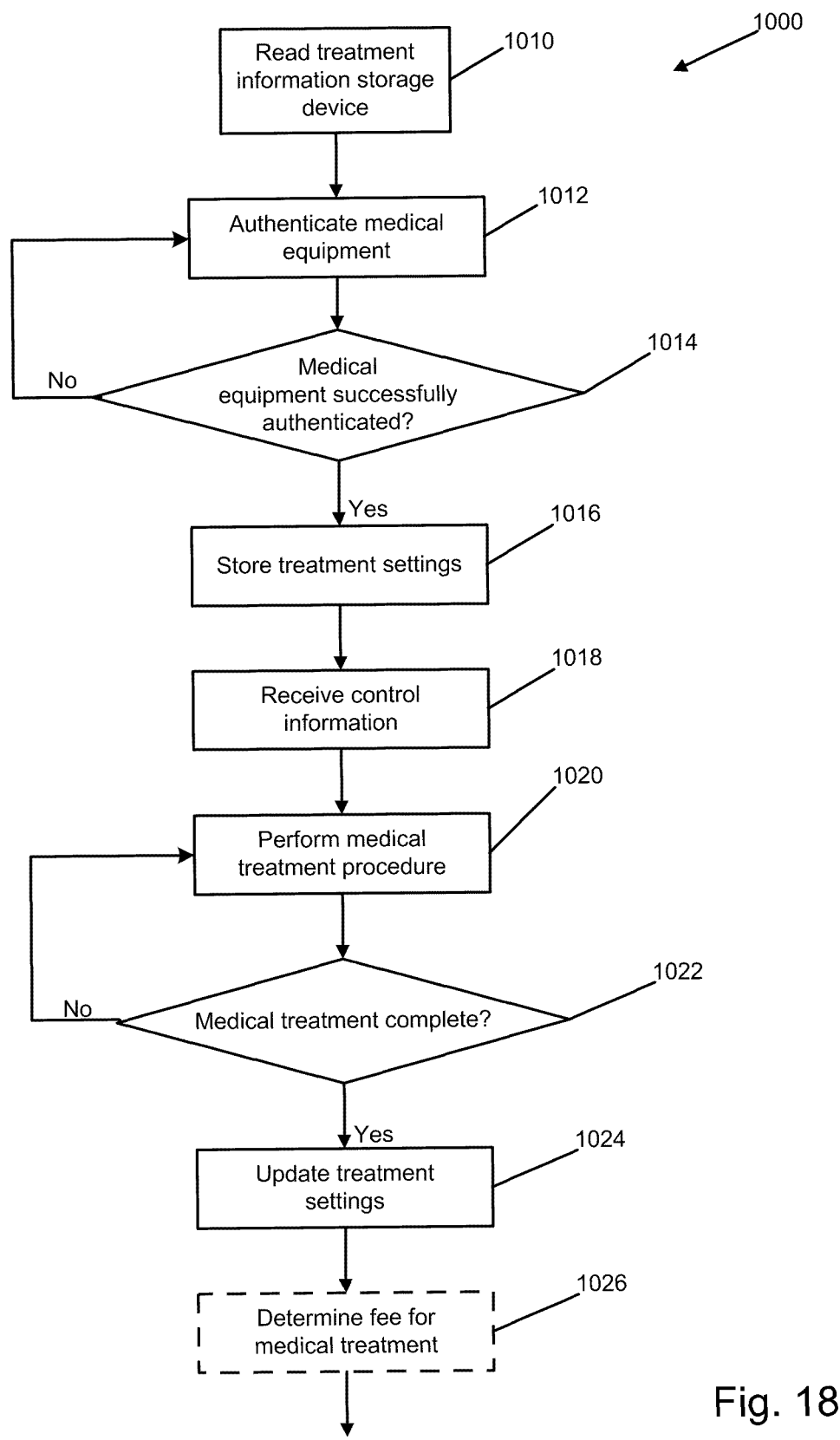
FIG. 18 is a flow diagram illustrating a method of operation of a medical system according to an embodiment of the invention.

FIGS. 16-18 are flowcharts illustrating methods of providing medical treatment using a medical treatment system according to embodiments of the invention.

Referring to FIG. 16, in step 810 of method 800, a controller configured to control an apparatus that is designed to perform a medical treatment performs initialization and is authenticated. The controller 120 may be authenticated with information such as a password that may be stored in a treatment information storage device.

In step 811, whether the controller is successfully authenticated is determined. If the controller is successfully authenticated, step 812 is performed. If the controller is not successfully authenticated, step 813 is performed.

In step 813, the controller is prevented from operating. In one embodiment, the controller may be prevented from operating by maintaining or changing a switch inside of the controller to an off mode.

In step 812, the controller is enabled to operate and/or one or more treatment settings are received. Step 812 may include one or more of storing previous treatment data, setting treatment area information, resetting and/or calculating a number of shock wave pulses and calculating treatment time and/or total treatment time. Steps 810, 811, 812, 813 may be a part of a security process providing secure access to the controller.

In step 814, a determination is made as to whether each of the treatment settings has been received. In some cases, each of the treatment settings has not been received and additional information may need to be received.

If it is determined that all of the treatment settings have not been received, the process goes to step 812. If each of the treatment settings is determined to have been received, the process goes to step 816. In step 816, information regarding the kit type is received. Step 816 may include one or more of reading or writing a treatment information storage device from a kit to determine the kit type.

In step 818, a determination is made as to whether the kit is acceptable. The kit type may be indicative of a size of a wound kit in some embodiments. If the wound kit corresponds to the patient wound size, and/or corresponds to a region in which the treatment is approved by the government for the region, information regarding the kit type is deemed acceptable. Otherwise, information regarding the kit type is deemed not acceptable.

If information regarding the kit type is not acceptable, the process goes back to step 816. If information regarding the kit type is acceptable, the process goes to step 820.

In step 820, medical treatment preparation is performed. Step 820 includes processing configuration information for configuring the medical treatment apparatus with the one or more of the treatment settings received. Step 820 may also include performing a security process to identify and/or ensure that the treatment information storage device is authentic and to ensure that any ancillary medical treatment device and/or any medical treatment apparatus are compatible and/or appropriate for the treatment.

In step 822, medical treatment is provided to a patient. Step 822 may include providing a treatment consisting of a number of shock wave pulses or for a time period as designated by the treatment settings.

In step 824, a determination is made as to whether the medical treatment has been completed. In some embodiments, the medical treatment is determined to have been completed if the number of shock waves designated to be provided to the patient for the medical treatment has been provided or if the total time designated for the medical treatment has elapsed.

If the medical treatment is determined to have been completed, in step 826, the data indicative of the treatment provided is stored in a memory of the controller and the medical treatment ceases. The process then continues with step 828. If the medical treatment is determined to not have been completed, the medical treatment continues in accordance with step 822.

In step 828, a determination is made as to whether a new treatment is to be provided. If a determination is made that a new treatment is not to be provided, the process continues to step 830. In step 830, the apparatus for controlling the medical treatment or the apparatus for performing the medical treatment performs shut-down operations. Shut-down operations may include writing treatment data and performing a soft shut-off of the apparatus. Shut down operations may also include tabulating treatment data including, but not limited to, energy settings, number and frequency of shocks provided and the type of medical treatment apparatus and/or ancillary treatment apparatus used.

If a determination is made that a new treatment is to be provided, the process continues to step 812 and treatment settings are again received. Method 800 follows the subsequent steps as described with regard to and illustrated above in FIG. 16.

Referring to FIG. 17, a method 900 may be performed as illustrated. The method 900 is incorporated by reference herein in its entirety.

Referring to FIG. 18, in some embodiments, the method 1000 may be performed as follows. In step 1010, a treatment information storage device is read by a reader. In various embodiments, the reader may be an optical reader, an RFID reader, label and/or chip reader, a barcode reader, a magnetic stripe reader or any mechanism configured to access and read information stored on the treatment information storage device. For example, the treatment information storage device may be accessed upon being inserted into a recess of the reader and the information stored on the treatment storage device may subsequently read.

In step 1012, the controller and/or the medical treatment apparatus used to perform the medical procedure may be authenticated.

In one embodiment, step 1012 includes determining the type of prospective medical treatment apparatus and/or controller to be used in the procedure, determining the required medical treatment apparatus and/or controller as stored on the treatment storage device. If the type of prospective medical treatment apparatus and/or controller is the same as the required medical treatment apparatus and/or controller, the medical treatment apparatus and/or controller is authenticated.

A similar process may be provided by comparing the ancillary treatment apparatus presented as the presumptive kit component to the required ancillary treatment apparatus to determine if the presumptive ancillary treatment apparatus is proper. If the comparison indicates that the required medical equipment is the same as the presumptive medical equipment, the presumptive medical equipment is authenticated and may be used during the procedure. Accordingly, the process provides a solution to address the problem of using generic substitute devices and/or incompatible devices for treatment.

In step 1014, it is determined whether the medical equipment was successfully authenticated. If not, the process goes back to step 1012. If so, in step 1016, one or more treatment settings that were stored on the treatment information storage device are stored in the memory of the controller configured to control the treatment. With reference to 1 and 8, in step 1016, the treatment settings may be stored on the controller 120, controller subsystem 220, medical treatment apparatus 130 or medical treatment subsystem 230.

Referring back to FIG. 18, the one or more treatment settings may include information such as the treatments to provide to the patient, the length of time for each of the treatments, the total length of time for all treatments combined, a number of shock waves to apply to the patient in a treatment or over all treatments combined, a frequency at which to apply the shock waves to the patient, and/or an energy setting of the medical treatment apparatus.

In step 1018, control information for controlling the medical treatment apparatus is received at the medical treatment apparatus. The control information may be generated by the controller as a result of the information read from the treatment storage device. The control information may be generated after the controller is authenticated. The generated information may be transmitted to and received by the medical treatment apparatus.

In step 1020, the medical treatment procedure is performed in accordance with the one or more of the treatment settings. In one embodiment, the medical procedure is performed by utilizing the medical treatment apparatus to provide a selected number of shock waves to the patient at a selected frequency for a selected length of time, at a selected energy setting. In another embodiment, parameters indicative of the medical procedure may be so low as to prevent any medical procedure from being performed. Such may be the case if the treatment storage device has been used to obtain previous treatments and the device now needs to have additional value added to the treatment information storage device. For example, the number of shock waves to be applied may be zero and, accordingly, no medical treatment procedure will be performed.

In step 1022, a determination is made as to whether the medical treatment is complete. In one embodiment, a number of shocks or a time for the medical procedure may be identified at the beginning of the medical procedure. The number of remaining shock waves to be applied or the remaining time duration for the medical treatment may be decreased after one or more shock waves have been applied or a portion of time has elapsed. With reference to 1 and 8, the medical treatment apparatus 130, medical treatment subsystem 230, controller 120 or controller subsystem 220 may keep a record of outstanding shock waves or time duration and determine that the treatment is complete when no more shock waves or time remains for the treatment.

If the medical treatment is not complete, the medical treatment continues to be performed as the process goes to step 1020. If the medical treatment is complete, in step 1024, the one or more treatment settings are updated based on the treatment provided in step 1020 and/or based on value added to the treatment information storage device. In one embodiment, a total time for a series of medical treatments may be decremented by a length of time of one or more previous or current medical treatments that has been performed. In some embodiments, the treatment storage device may be re-charged or updated with additional treatment time, number of shocks, etc. by adding additional value to the treatment storage device. Additional value may be added by any number of ways, including, but not limited to, causing a repository to associate a high dollar value with the treatment storage device in connection with money or insurance benefits provided in association with the treatment information storage device.

In one embodiment of method 1000, as shown in step 1026, a fee for the medical treatment may optionally be determined. The fee may be determined in accordance with the method 1100 described in FIG. 19.

The process of method 1000 may be repeated any number of times as long as the treatment settings indicate that at least one treatment remains and is allowed. In some embodiments, the process may be repeated to provide the medical procedure only after a certain time interval has elapsed since a previous medical treatment. In this regard, the likelihood of overtreating a patient may be reduced.

FIG. 19 is a flowchart illustrating a method of fee provisioning according to an embodiment of the present invention. In step 1110, one or more treatment settings are identified.

In step 1112, the one or more identified treatment settings are assigned a value. The value may be a fee associated with each treatment setting or a fee associated with a number of treatment settings.

In step 1114, a type of ancillary treatment apparatus to be used in providing the medical treatment designated by the treatment settings is determined for a treatment apparatus. In step 1116, the type of ancillary treatment apparatus is assigned a value. The value may be any information indicative of or that can be correlated to a monetary fee. Method 1100 may optionally include a step 1118 for incorporating one or more discounts in a total value. The discount may be a negotiated insurance rate or a discount offered by the medical facility or medical personnel. The discount may be a coupon or other value currently or previously provided by the patient. As noted above, the discount may be incorporated at step 1118.

In step 1120, a fee corresponding to the medical treatment is determined. In the embodiments wherein the values assigned in steps 1112 and 1114 are monetary values, the fee may be determined by adding the monetary values and subtracting from a total monetary value any discounts incorporated in step 1118. Method 1100 may optionally continue by displaying the determined fee in step 1122. With reference to FIG. 1, in some embodiments, display 126 may be configured to display an image indicative of the fee determined in step 1120.

In various embodiments, methods for calculating fees for medical treatments based on ancillary treatment apparatus and/or treatment settings for a medical procedure may be done based on a certain value for each device and/or based solely on the type of medical treatment. It is important to know if the kit is sold directly to the hospital or through a distributor, because the dollar amount may be different. The kit cost may also differ based on the region (for example discount prices for markets that have in general lower income per capita—eastern part of a continent or country compared with western part of a continent or country).

Accordingly, in some embodiments a fee may be provided that is a function of the values of the one or more treatment settings and/or the ancillary treatment apparatus. In this regard, for example, a medical treatment providing 2500 shock waves may determine that a greater fee for the medical treatment is required than the fee for a medical treatment providing 500 shock waves. Further, a medical treatment using a reusable ancillary treatment apparatus may determine a lower fee for the medical treatment than a medical treatment using a disposable ancillary treatment apparatus. Methods for calculating fees may be as provided herein or by any of the well-known methods for determining fees for medical treatments known to those in the art.

Some embodiments of the invention include a computer program product. The computer program product may include a computer-readable medium having computer-readable program code stored thereon. The computer-readable program code of the computer-readable medium may be accessed by a processor and cause the processor to execute one or more of the methods described herein. Any processor capable of reading computer-readable program code and executing the instructions thereof may be used.

In one embodiment, the computer-readable program code may be accessed by the processor and cause the processor to execute one or more of the methods described herein. In various embodiments, the computer program product may be executed by a processor to perform the steps of methods 800, 900, 1000 or 1100 or substeps thereof.

The foregoing description of embodiments of the invention has been presented for purposes of illustration. It is not intended to be exhaustive or to limit the invention to the precise form disclosed, and modifications and variations are possible in light of the above teaching or may be acquired from practice of the invention. The embodiments were chosen and described in order to explain the principles of embodiments of the invention and its practical application. Additionally, in the embodiments shown, one or more subsystems of systems may be combined into a single subsystem or may be segmented physically or operationally into additional subsystems. The systems and subsystems may be located at a location that is proximate to or geographically remote from any other subsystem.

Further, the operations of one or more methods steps may be performed in a single step or performed in numerous additional steps beyond that shown and discussed. Additionally, it should be noted that although the flowcharts provided herein show specific orders of method steps, it is understood that the orders of steps may differ from what is depicted. Also, the steps could be performed concurrently or with partial concurrence. All such variations are within the scope of the invention.

Finally, values described in the embodiments of the invention are merely exemplary and, as known by those of ordinary skill in the art, may be modified as desired while still remaining within the spirit and scope of embodiments of the invention.

What is claimed is:

1. A medical treatment system comprising:
    an input device operatively coupled to an electronic controller, wherein the input device comprises a physical data input device operatively coupled to the electronic controller;
    the electronic controller including a microprocessor and a microprocessor-readable data storage medium having microprocessor-executable instructions configured to determine specific medical treatment control parameters to apply for treatment of a body target location based on at least one of physical, anatomical and medical characteristics of the body target location received from the input device and configured to apply the specific medical treatment control parameters to an electronic medical treatment apparatus operatively coupled to the electronic controller;
    an ancillary treatment apparatus configured as an interface between a patient and the electronic medical treatment apparatus for use under the specific medical treatment control parameters, and wherein the electronic controller includes a microprocessor-readable data storage medium having microprocessor-executable instructions configured to display that the ancillary treatment apparatus should be selected from among a plurality of available ancillary treatment apparatuses based on medical treatment data received from the physical data input device;
    a physical ancillary data storage medium packaged together with the ancillary treatment apparatus and packaged independent of the electronic medical treatment apparatus, wherein the physical ancillary data storage medium is configured with predetermined further instructions that provide authentication to the electronic controller that the ancillary treatment apparatus is authorized for use with at least one of application of the specific medical treatment control parameters and the electronic medical treatment apparatus;
    a data reader configured for reading the predetermined further instructions of the ancillary data storage medium, wherein the data reader is operatively coupled to the microprocessor of the electronic controller; and
    a display operatively coupled to the microprocessor of the electronic controller, wherein a microprocessor-readable data storage medium of the electronic controller is configured with instructions executable by the microprocessor of the electronic controller that provide a visual confirmation on the display that the electronic medical treatment apparatus is activated for use after the data reader reads the predetermined further instructions from the ancillary data storage medium and authorization of use of the ancillary treatment apparatus has been authenticated.

2. The medical treatment system of claim 1, wherein the electronic medical treatment apparatus is an acoustic pressure wave device.

3. The medical treatment system of claim 2, wherein the acoustic pressure wave device is a shock wave device.

4. The medical treatment system of claim 3, wherein the ancillary treatment apparatus is selected from the group consisting of a sleeve, a pad, sterility barrier coupling gel, drug delivery device, drape, reflector, lens and an applicator head.

5. The medical treatment system of claim 1, wherein the electronic controller includes a microprocessor-readable data storage medium including microprocessor-readable instructions configured to visually confirm on the display that information for a treatment area of a body received from the physical data input device is compatible with treatment by the electronic medical treatment apparatus according to the predetermined further instructions contained on the physical ancillary data storage medium.

6. The medical treatment system of claim 5, wherein the electronic medical treatment apparatus is an acoustic pressure wave device and the information for a treatment area of a body includes a measurement selected from the group consisting of a dimension of a wound and a volume of body target location.

7. The medical treatment system of claim 2, wherein the electronic controller includes a microprocessor-readable data storage medium including microprocessor-readable instructions configured to visually confirm on the display that a body part identification received from the physical data input device is compatible with treatment by the electronic medical treatment apparatus according to the predetermined further instructions contained on the physical ancillary data storage medium.

8. The medical treatment system of claim 2, wherein the electronic controller includes a microprocessor-readable data storage medium including microprocessor-readable instructions configured to visually confirm on the display that a medical condition identification received from the physical data input device is compatible with treatment by the electronic medical treatment apparatus according to the predetermined further instructions contained on the physical ancillary data storage medium.

9. The medical treatment system of claim 2, wherein the ancillary treatment apparatus is selected from the group consisting of a sleeve, a pad, sterility barrier, coupling gel, drug delivery device, drape, reflector, lens and an applicator head.

10. The medical treatment system of claim 9, wherein the medical treatment data includes a measurement selected from the group consisting of length of a wound, diameter of a wound, depth of a wound, length of a wound, width of a wound and a volume of body target location.

11. The medical treatment system of claim 9, wherein the medical treatment data includes at least one of a body part identification, tissue identification and organ identification.

12. The medical treatment system of claim 9, wherein the medical treatment data includes at least one of a medical condition identification and status of a medical condition.

13. The medical treatment system of claim 1, wherein the medical treatment data includes one or more dimensions of a body target location.

14. The medical treatment system of claim 1, wherein the medical treatment data includes at least one of a body part identification, tissue identification and organ identification.

15. The medical treatment system of claim 1, wherein the medical treatment data includes at least one of a medical condition identification and status of a medical condition.

16. The medical treatment system of claim 1, wherein the physical ancillary data storage medium includes a radio frequency identification readable medium and the data reader is a radio frequency identification reader.

17. The medical treatment system of claim 2, wherein the physical ancillary data storage medium includes a radio frequency identification readable medium and the data reader is a radio frequency identification reader.

18. The medical treatment system of claim 17, wherein a microprocessor-readable data storage medium of the electronic controller includes microprocessor-executable instructions configured to apply specific medical treatment control parameters to a medical treatment apparatus operatively coupled to the electronic controller from receipt of predetermined further instructions for applying the specific medical treatment control parameters contained on the physical ancillary data storage medium.

19. The medical treatment system of claim 1, wherein a microprocessor-readable data storage medium of the electronic controller includes microprocessor-executable instructions configured to apply specific medical treatment control parameters to a medical treatment apparatus operatively coupled to the electronic controller from receipt of predetermined further instructions for applying the specific medical treatment control parameters contained on the physical ancillary data storage medium.

20. The medical treatment system of claim 2, wherein a microprocessor-readable data storage medium of the electronic controller includes microprocessor-executable instructions configured to apply specific medical treatment control parameters to a medical treatment apparatus operatively coupled to the electronic controller from receipt of predetermined further instructions for applying the specific medical treatment control parameters contained on the physical ancillary data storage medium.

21. The medical treatment system of claim 20, wherein the predetermined further instructions for applying the specific medical treatment control parameters contained on the physical ancillary data storage medium include one or more parameters selected from the group consisting of number of treatments, length of time of each treatment, total length of treatment time, number of shock to apply in each treatment, total number of shocks, frequency, energy setting, treatment area, treatment penetration depth, ancillary treatment apparatus identification, medical treatment apparatus identification, controller identification and geographic region identification.

22. The medical treatment system of claim 1, wherein the physically ancillary data storage medium includes instructions configured to enable processing by electronic controller to carry out one or more of tracking inventory of ancillary treatment apparatuses, performing inventory control functions, reducing theft, fee provisioning, insurance coding, paying invoices, fee reimbursements, decreasing available treatment and replenishing available treatments.

* * * * *